Figure 3A:
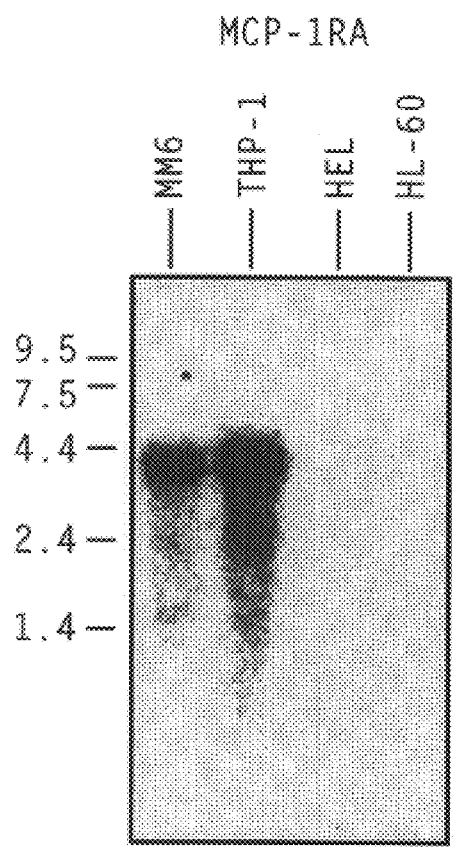

United States Patent [19]
Charo et al.

[11] Patent Number: 6,132,987
[45] Date of Patent: *Oct. 17, 2000

[54] RECOMBINANT MAMMALIAN MONOCYTE CHEMOTACTIC PROTEIN-1 (MCP-1) RECEPTORS (MCP-1R, CCR-2)

[75] Inventors: Israel F. Charo, Lafayette; Shaun R. Coughlin, Tiburon, both of Calif.

[73] Assignee: The Regents of the University of California, Oakland, Calif.

[*] Notice: This patent is subject to a terminal disclaimer.

[21] Appl. No.: 08/446,669

[22] PCT Filed: Jan. 11, 1995

[86] PCT No.: PCT/US95/00476

§ 371 Date: May 25, 1995

§ 102(e) Date: May 25, 1995

[87] PCT Pub. No.: WO95/19436

PCT Pub. Date: Jul. 20, 1995

Related U.S. Application Data

[63] Continuation-in-part of application No. 08/182,962, Jan. 13, 1994, abandoned.

[51] Int. Cl.$^7$ .................. C12N 15/12; C07K 14/715; G01N 33/53
[52] U.S. Cl. .................. 435/69.1; 536/23.5; 530/350; 514/2; 435/320.1; 435/325; 435/252.3; 435/254.11; 435/7.1; 435/7.21; 435/348
[58] Field of Search .................. 536/23.5; 530/350; 435/69.1, 320.1, 325, 252.3, 254.4, 7.1, 7.21, 348; 514/1, 2

[56] References Cited

U.S. PATENT DOCUMENTS

| | | | |
|---|---|---|---|
| 5,459,128 | 10/1995 | Rollins et al. | 514/8 |
| 5,460,955 | 10/1995 | Mosher et al. | 435/69.7 |
| 5,547,854 | 8/1996 | Donahoe et al. | 435/69.1 |
| 5,707,815 | 1/1998 | Charo et al. | 435/7.2 |

FOREIGN PATENT DOCUMENTS

94/07542  4/1994  WIPO .

OTHER PUBLICATIONS

Ansubel, F.M., *Current Protocols in Molecular Biology*, Wiley & Sons, New York 1:22–32, pp. 6.11.11–6.11.16 (1994).

Yamagami, S. et al., cDNA cloning and functional expression of a human monocyte chemoattractant protein 1 receptor, Biochem. Biophys. Res. Comm., vol. 202, 2:1156–1162 (Jul. 29, 1994).

Ylä–Herttuala et al., "Expression of monocyte chemoattractant protein 1 in macrophage–rich areas of human and rabbit atherosclerotic lesions" (1991) *Proc. Natl. Acad. Sci.* 88:5252–5256.

Cushing et al., "Minimally modified low density lipoprotein induces monocyte chemotatcic protein 1 in human endothelial cells and smooth muscle celss" (1990) *Proc. Natl. Acad. Sci.* 87:5134–5138.

Holmes et al., "Structure and Functional Expression of a Human Interleukin–8 Receptor" (1991) *Science* 253:1278–1280.

Murphy, P.M. and Tiffany, H.L., "Cloning of Complementary DNA Encoding a Functional Human Interleukin–8 Receptor" (1991) *Science* 253:1280–1283.

Gao, et al., "Structure and Functional Expression of the Human Macrophage Inflammatory Protein 1α/RANTES Receptor" (1993) *The Journal of Experimental Medicine* 177:1421–1427.

Neote, et al., "Molecular Cloning, Functional Expression, and Signaling Characteristics of a C–C Chemokine Receptor" (1993) *Cell* 72:415–425.

Edgington, S.M., "Chemokines In Cardiovascular Disease" (1993) *Bio/Technology* 11:676–681.

Yoshimura, et al., "Purification and Amino Acid Analysis of Two Human Glioma–Derived Monocyte Chemoattractants" (1989) *The Journal of Experimental Medicine* 169:1449–1459.

Furutani, et al., "Cloning and Sequencing of the c DNA For Human Monocyte Chemotactic and Activating Factor (MCAF)" (1989) *Biochemical and Biophysical Research Communications* 159(1):249–255.

Faggiotto, et al., "Studies of Hypercholesterolemia in the Nonhuman Primate—I. Changes that Lead to Fatty Streak Formation" (1984) *Arteriosclerosis* 4(4):323–340.

Watson, S. et al., eds. *The G–Protein Linked Receptor—Facts Book*, London, Academic Press (1994) Introduction, pp. 2–6.

Gearing, David P. et al., "Expression Cloning of a Receptor for Human Granulocyte–Macrophage Colony–Stimulating Factor" (1989) 8(12)3667–3676.

Van Riper et al., "Characterization and Species Distribution of HIgh Affinity GTP–coupled Receptors for Human Rantes and Monocyte Chemoattractant Protein 1" (1993) *J. Exp. Med.* 177:851–856.

Wang et al., "Identification of RANTES Receptors on Human Monocytic Cells: Competition for Binding and Desensitization by Homologous Chemotactic Cytokines" (1993) *The Journal of Experimental Medicine* 177:699–705.

Wolpe, S.D. and Cerami, A., "Macrophage inflammatory proteins 1 and 2: members of a novel superfamily of cytokines" (1989) *The FASEB Journal* 3:2565–2573.

Oppenheim et al., "Properties of Genes and Gene Products of the Intercrine Family" (1991) *Annual Review of Immunology* 9:620–648.

(List continued on next page.)

*Primary Examiner*—David L. Fitzgerald
*Attorney, Agent, or Firm*—Townsend and Townsend and Crew LLP

[57] ABSTRACT

DNAs encoding receptors for the chemokine, Monocyte Chemotactic Protein-1 (MCP-1), are disclosed. Recombinant reagents and methods for expressing the DNAs are also provided. Exemplary receptor proteins are MCP-1RA and MCP-1RB, which correspond to alternatively spliced transcripts of the human MCP-1R gene. The receptor proteins of the invention are useful in assays to identify agonists and antagonists of MCP-1.

28 Claims, 14 Drawing Sheets

OTHER PUBLICATIONS

Rollins, B.J. and Sunday, M.E., "Suppression of Tumor Formation In Vivo by Expression of the JE Gene in Malignant Cells" (1991) *Molecular and Cellular Biology* 11(6):3125–3131.

Walter et al., "Macrophage Infiltration and Growth of Sarcoma Clones Expressing Different Amounts of Monocyte Chemotactic Protein/JE" (1991) *Int. J. Cancer* 49:431–435.

Koch et al., "Enhanced Production of Monocyte Chemoattractant Protein–1 in Rheumatoid Arthritis" (1992) *The Journal of Clinical Investigation, Inc.* 90:772–779.

Jones et al., "Potential Role of Monocyte Chemoattractant Protein 1/JE in Monocyte/Macrophage–Dependent IgA Immune Complex Alveolitis in the Rat" (1992) *The Journal of Immunology* 149:2147–2154.

Nelken et al., "Monocyte Chemoattractant Protein–1 in Human Atheromatous Plaques" (1991) *J. Clin. Invest.* 88:1121–1127.

Charo et al *Proc. Nat'l. Acad. Sci USA* vol. 91 pp. 2752–2756 (1994).

Beall, C. J., et al. (1992) *J. Biol. Chem.* 267:3455–59.

FIG. 1A

| | |
|---|---|
| GGATTGAACA AGGACGCATT TCCCCAGTAC ATCCACAAC ATG CTG TCC ACA TCT<br>                                                           Met Leu Ser Thr Ser<br>                                                           1                 5 | 54 |
| CGT TCT CGG TTT ATC AGA AAT ACC AAC GAG AGC GGT GAA GAA GTC ACC<br>Arg Ser Arg Phe Ile Arg Asn Thr Asn Glu Ser Gly Glu Glu Val Thr<br>              10                                  15          20 | 102 |
| ACC TTT TTT GAT TAT GAT TAC GGT GCT CCC TGT CAT AAA TTT GAC GTG<br>Thr Phe Phe Asp Tyr Asp Tyr Gly Ala Pro Cys His Lys Phe Asp Val<br>        25                     30                  35 | 150 |
| AAG CAA ATT GGG GCC CAA CTC CTG CCT CCG CTC TAC TCG CTG GTG TTC<br>Lys Gln Ile Gly Ala Gln Leu Leu Pro Pro Leu Tyr Ser Leu Val Phe<br>        40                     45                  50 | 198 |
| ATC TTT GGT TTT GTG GGC AAC ATG CTG GTC GTC CTC ATC TTA ATA AAC<br>Ile Phe Gly Phe Val Gly Asn Met Leu Val Val Leu Ile Leu Ile Asn<br>        55                     60                  65 | 246 |
| TGC AAA AAG CTG AAG TGC TTG ACT GAC ATT TAC CTG CTC AAC CTG GCC<br>Cys Lys Lys Leu Lys Cys Leu Thr Asp Ile Tyr Leu Leu Asn Leu Ala<br>        70                     75                  80                  85 | 294 |
| ATC TCT GAT CTG CTT TTT CTT ATT ACT CTC CCA TTG TGG GCT CAC TCT<br>Ile Ser Asp Leu Leu Phe Leu Ile Thr Leu Pro Leu Trp Ala His Ser<br>                 90                     95                 100 | 342 |
| GCT GCA AAT GAG TGG GTC TTT GGG AAT GCA ATG TGC AAA TTA TTC ACA<br>Ala Ala Asn Glu Trp Val Phe Gly Asn Ala Met Cys Lys Leu Phe Thr<br>               105                    110                 115 | 390 |
| GGG CTG TAT CAC ATC GGT TAT TTT GGC GGA ATC TTC TTC ATC ATC CTC<br>Gly Leu Tyr His Ile Gly Tyr Phe Gly Gly Ile Phe Phe Ile Ile Leu<br>             120                    125                 130 | 438 |
| CTG ACA ATC GAT AGA TAC CTG GCT ATT GTC CAT GCT GTG TTT GCT TTA<br>Leu Thr Ile Asp Arg Tyr Leu Ala Ile Val His Ala Val Phe Ala Leu<br>         135                    140                 145 | 486 |

FIG. 1B

| | |
|---|---|
| AAA GCC AGG ACG GTC ACC TTT GGG GTG GTG ACA AGT GTG ATC ACC TGG<br>Lys Ala Arg Thr Val Thr Phe Gly Val Val Thr Ser Val Ile Thr Trp<br>150                  155                160              165 | 534 |
| TTG GTG GCT GTG TTT GCT TCT GTC CCA GGA ATC ATC TTT ACT AAA TGC<br>Leu Val Ala Val Phe Ala Ser Val Pro Gly Ile Ile Phe Thr Lys Cys<br>                170                175              180 | 582 |
| CAG AAA GAA GAT TCT GTT TAT GTC TGT GGC CCT TAT TTT CCA CGA GGA<br>Gln Lys Glu Asp Ser Val Tyr Val Cys Gly Pro Tyr Phe Pro Arg Gly<br>                185                190              195 | 630 |
| TGG AAT AAT TTC CAC ACA ATA ATG AGG AAC ATT TTG GGG CTG GTC CTG<br>Trp Asn Asn Phe His Thr Ile Met Arg Asn Ile Leu Gly Leu Val Leu<br>        200                205              210 | 678 |
| CCG CTG CTC ATC ATG GTC ATC TGC TAC TCG GGA ATC CTG AAA ACC CTG<br>Pro Leu Leu Ile Met Val Ile Cys Tyr Ser Gly Ile Leu Lys Thr Leu<br>        215                220              225 | 726 |
| CTT CGG TGT CGA AAC GAG AAG AAG AGG CAT AGG GCA GTG AGA GTC ATC<br>Leu Arg Cys Arg Asn Glu Lys Lys Arg His Arg Ala Val Arg Val Ile<br>230                  235                240              245 | 774 |
| TTC ACC ATC ATG ATT GTT TAC TTT CTC TTC TGG ACT CCC TAT AAC ATT<br>Phe Thr Ile Met Ile Val Tyr Phe Leu Phe Trp Thr Pro Tyr Asn Ile<br>                250                255              260 | 822 |
| GTC ATT CTC CTG AAC ACC TTC CAG GAA TTC TTC GGC CTG AGT AAC TGT<br>Val Ile Leu Leu Asn Thr Phe Gln Glu Phe Phe Gly Leu Ser Asn Cys<br>        265                270              275 | 870 |
| GAA AGC ACC AGT CAA CTG GAC CAA GCC ACG CAG GTG ACA GAG ACT CTT<br>Glu Ser Thr Ser Gln Leu Asp Gln Ala Thr Gln Val Thr Glu Thr Leu<br>        280                285              290 | 918 |
| GGG ATG ACT CAC TGC TGC ATC AAT CCC ATC ATC TAT GCC TTC GTT GGG<br>Gly Met Thr His Cys Cys Ile Asn Pro Ile Ile Tyr Ala Phe Val Gly<br>295                  300                305 | 966 |

FIG. 1C

| | |
|---|---|
| GAG AAG TTC AGA AGC CTT TTT CAC ATA GCT CTT GGC TGT AGG ATT GCC<br>Glu Lys Phe Arg Ser Leu Phe His Ile Ala Leu Gly Cys Arg Ile Ala<br>310                  315                320              325 | 1014 |
| CCA CTC CAA AAA CCA GTG TGT GGA GGT CCA GGA GTG AGA CCA GGA AAG<br>Pro Leu Gln Lys Pro Val Cys Gly Gly Pro Gly Val Arg Pro Gly Lys<br>                330                335              340 | 1062 |
| AAT GTG AAA GTG ACT ACA CAA GGA CTC CTC GAT GGT CGT GGA AAA GGA<br>Asn Val Lys Val Thr Thr Gln Gly Leu Leu Asp Gly Arg Gly Lys Gly<br>            345                350              355 | 1110 |
| AAG TCA ATT GGC AGA GCC CCT GAA GCC AGT CTT CAG GAC AAA GAA GGA<br>Lys Ser Ile Gly Arg Ala Pro Glu Ala Ser Leu Gln Asp Lys Glu Gly<br>            360                365              370 | 1158 |
| GCC TAGAGACAGA AATGACAGAT CTCTGCTTTG GAAATCACAC GTCTGGCTTC<br>Ala | 1121 |
| ACAGATGTGT GATTCACAGT GTGAATCTTG GTGTCTACGT TACCAGGCAG GAAGGCTGAG | 1271 |
| AGGAGAGAGA CTCCAGCTGG GTTGGAAAAC AGTATTTTCC AAACTACCTT CCAGTTCCTC | 1331 |
| ATTTTTGAAT ACAGGCATAG AGTTCAGACT TTTTTTAAAT AGTAAAAATA AAATTAAAGC | 1391 |
| TGAAAACTGC AACTTGTAAA TGTGGTAAAG AGTTAGTTTG AGTTGCTATC ATGTCAAACG | 1451 |
| TGAAAATGCT GTATTAGTCA CAGAGATAAT TCTAGCTTTG AGCTTAAGAA TTTTGAGCAG | 1511 |
| GTGGTATGTT TGGGAGACTG CTGAGTCAAC CCAATAGTTG TTGATTGGCA GGAGTTGGAA | 1571 |
| GTGTGTGATC TGTGGGCACA TTAGCCTATG TGCATGCAGC ATCTAAGTAA TGATGTCGTT | 1631 |
| TGAATCACAG TATACGCTCC ATCGCTGTCA TCTCAGCTGG ATCTCCATTC TCTCAGGCTT | 1691 |
| GCTGCCAAAA GCCTTTTGTG TTTTGTTTTG TATCATTATG AAGTCATGCG TTTAATCACA | 1751 |
| TTCGAGTGTT TCAGTGCTTC GCAGATGTCC TTGATGCTCA TATTGTTCCC TAATTTGCCA | 1811 |
| GTGGGAACTC CTAAATCAAA TTGGCTTCTA ATCAAAGCTT TTAAACCCTA TTGGTAAAGA | 1871 |

FIG. 1D

```
ATGGAAGGTG GAGAAGCTCC CTGAAGTAAG CAAAGACTTT CCTCTTAGTC GAGCCAAGTT    1931
AAGAATGTTC TTATGTTGCC CAGTGTGTTT CTGATCTGAT GCAAGCAAGA AACACTGGGC    1991
TTCTAGAACC AGGCAACTTG GGAACTAGAC TCCCAAGCTG GACTATGGCT CTACTTTCAG    2051
GCCACATGGC TAAAGAAGGT TTCAGAAAGA AGTGGGGACA GAGCAGAACT TTCACCTTCA    2111
TATATTTGTA TGATCCTAAT GAATGCATAA AATGTTAAGT TGATGGTGAT GAAATGTAAA    2171
TACTGTTTTT AACAACTATG ATTTGGAAAA TAAATCAATG CTATAACTAT GTTGATAAAA    2231
G                                                                   2232
```

FIG. 2A

| | |
|---|---|
| CAGGACTGCC TGAGACAAGC CACAAGCTGA ACAGAGAAAG TGGATTGAAC AAGGACGCAT | 60 |

```
TTCCCCAGTA CATCCACAAC ATG CTG TCC ACA TCT CGT TCT CGG TTT ATC              110
                     Met Leu Ser Thr Ser Arg Ser Arg Phe Ile
                       1               5                  10

AGA AAT ACC AAC GAG AGC GGT GAA GAA GTC ACC ACC TTT TTT GAT TAT            158
Arg Asn Thr Asn Glu Ser Gly Glu Glu Val Thr Thr Phe Phe Asp Tyr
             15                  20                  25

GAT TAC GGT GCT CCC TGT CAT AAA TTT GAC GTG AAG CAA ATT GGG GCC            206
Asp Tyr Gly Ala Pro Cys His Lys Phe Asp Val Lys Gln Ile Gly Ala
             30                  35                  40

CAA CTC CTG CCT CCG CTC TAC TCG CTG GTG TTC ATC TTT GGT TTT GTG            254
Gln Leu Leu Pro Pro Leu Tyr Ser Leu Val Phe Ile Phe Gly Phe Val
       45                  50                  55

GGC AAC ATG CTG GTC GTC CTC ATC TTA ATA AAC TGC AAA AAG CTG AAG            302
Gly Asn Met Leu Val Val Leu Ile Leu Ile Asn Cys Lys Lys Leu Lys
       60                  65                  70

TGC TTG ACT GAC ATT TAC CTG CTC AAC CTG GCC ATC TCT GAT CTG CTT            350
Cys Leu Thr Asp Ile Tyr Leu Leu Asn Leu Ala Ile Ser Asp Leu Leu
 75                  80                  85                  90

TTT CTT ATT ACT CTC CCA TTG TGG GCT CAC TCT GCT GCA AAT GAG TGG            398
Phe Leu Ile Thr Leu Pro Leu Trp Ala His Ser Ala Ala Asn Glu Trp
             95                 100                 105

GTC TTT GGG AAT GCA ATG TGC AAA TTA TTC ACA GGG CTG TAT CAC ATC            446
Val Phe Gly Asn Ala Met Cys Lys Leu Phe Thr Gly Leu Tyr His Ile
            110                 115                 120

GGT TAT TTT GGC GGA ATC TTC TTC ATC ATC CTC CTG ACA ATC GAT AGA            494
Gly Tyr Phe Gly Gly Ile Phe Phe Ile Ile Leu Leu Thr Ile Asp Arg
            125                 130                 135

TAC CTG GCT ATT GTC CAT GCT GTG TTT GCT TTA AAA GCC AGG ACG GTC            542
Tyr Leu Ala Ile Val His Ala Val Phe Ala Leu Lys Ala Arg Thr Val
            140                 145                 150
```

FIG. 2B

| | |
|---|---|
| ACC TTT GGG GTG GTG ACA AGT GTG ATC ACC TGG TTG GTG GCT GTG TTT<br>Thr Phe Gly Val Val Thr Ser Val Ile Thr Trp Leu Val Ala Val Phe<br>155                     160                     165                     170 | 590 |
| GCT TCT GTC CCA GGA ATC ATC TTT ACT AAA TGC CAG AAA GAA GAT TCT<br>Ala Ser Val Pro Gly Ile Ile Phe Thr Lys Cys Gln Lys Glu Asp Ser<br>                175                     180                     185 | 638 |
| GTT TAT GTC TGT GGC CCT TAT TTT CCA CGA GGA TGG AAT AAT TTC CAC<br>Val Tyr Val Cys Gly Pro Tyr Phe Pro Arg Gly Trp Asn Asn Phe His<br>                190                     195                     200 | 686 |
| ACA ATA ATG AGG AAC ATT TTG GGG CTG GTC CTG CCG CTG CTC ATC ATG<br>Thr Ile Met Arg Asn Ile Leu Gly Leu Val Leu Pro Leu Leu Ile Met<br>                205                     210                     215 | 734 |
| GTC ATC TGC TAC TCG GGA ATC CTG AAA ACC CTG CTT CGG TGT CGA AAC<br>Val Ile Cys Tyr Ser Gly Ile Leu Lys Thr Leu Leu Arg Cys Arg Asn<br>                220                     225                     230 | 782 |
| GAG AAG AAG AGG CAT AGG GCA GTG AGA GTC ATC TTC ACC ATC ATG ATT<br>Glu Lys Lys Arg His Arg Ala Val Arg Val Ile Phe Thr Ile Met Ile<br>235                     240                     245                     250 | 830 |
| GTT TAC TTT CTC TTC TGG ACT CCC TAT AAC ATT GTC ATT CTC CTG AAC<br>Val Tyr Phe Leu Phe Trp Thr Pro Tyr Asn Ile Val Ile Leu Leu Asn<br>                255                     260                     265 | 878 |
| ACC TTC CAG GAA TTC TTC GGC CTG AGT AAC TGT GAA AGC ACC AGT CAA<br>Thr Phe Gln Glu Phe Phe Gly Leu Ser Asn Cys Glu Ser Thr Ser Gln<br>                270                     275                     280 | 926 |
| CTG GAC CAA GCC ACG CAG GTG ACA GAG ACT CTT GGG ATG ACT CAC TGC<br>Leu Asp Gln Ala Thr Gln Val Thr Glu Thr Leu Gly Met Thr His Cys<br>                285                     290                     295 | 974 |
| TGC ATC AAT CCC ATC ATC TAT GCC TTC GTT GGG GAG AAG TTC AGA AGG<br>Cys Ile Asn Pro Ile Ile Tyr Ala Phe Val Gly Glu Lys Phe Arg Arg<br>                300                     305                     310 | 1022 |

FIG. 2C

```
TAT CTC TCG GTG TTC TTC CGA AAG CAC ATC ACC AAG CGC TTC TGC AAA      1070
Tyr Leu Ser Val Phe Phe Arg Lys His Ile Thr Lys Arg Phe Cys Lys
315             320             325             330

CAA TGT CCA GTT TTC TAC AGG GAG ACA GTG GAT GGA GTG ACT TCA ACA      1118
Gln Cys Pro Val Phe Tyr Arg Glu Thr Val Asp Gly Val Thr Ser Thr
                335             340             345

AAC ACG CCT TCC ACT GGG GAG CAG GAA GTC TCG GCT GGT TTA              1160
Asn Thr Pro Ser Thr Gly Glu Gln Glu Val Ser Ala Gly Leu
            350             355             360

TAAAACGAGG AGCAGTTTGA TTGTTGTTTA TAAAGGGAGA TAACAATCTG TATATAACAA    1220
CAAACTTCAA GGGTTTGTTG AACAATAGAA ACCTGTAAAG CAGGTGCCCA GGAACCTCAG    1280
GGCTGTGTGT ACTAATACAG ACTATGTCAC CAATGCATA  TCCAACATGT GCTCAGGGAA    1340
TAATCCAGAA AAACTGTGGG TAGAGACTTT GACTCTCCAG AAAGCTCATC TCAGCTCCTG    1400
AAAAATGCCT CATTACCTTG TGCTAATCCT CTTTTTCTAG TCTTCATAAT TTCTTCACTC    1460
AATCTCTGAT TCTGTCAATG TCTTGAAATC AAGGGCCAGC TGGAGGTGAA GAAGAGAATG    1520
TGACAGGCAC AGATGAATGG GAGTGAGGGA TAGTGGGGTC AGGGCTGAGA GGAGAAGGAG    1580
GGAGACATGA GCATGGCTGA GCCTGGACAA AGACAAAGGT GAGCAAAGGG CTCACGCATT    1640
CAGCCAGGAG ATGATACTGG TCCTTAGCCC CATCTGCCAC GTGTATTTAA CCTTGAAGGG    1700
TTCACCAGGT CAGGGAGAGT TTGGGAACTG CAATAACCTG GGAGTTTTGG TGGAGTCCGA    1760
TGATTCTCTT TTGCATAAGT GCATGACATA TTTTTGCTTT ATTACAGTTT ATCTATGGCA    1820
CCCATGCACC TTACATTTGA AATCTATGAA ATATCATGCT CCATTGTTCA GATGCTTCTT    1880
AGGCCACATC CCCCTGTCTA AAAATTCAGA AAATTTTTGT TTATAAAAGA TGCATTATCT    1940
ATGATATGCT AATATATGTA TATGCAATAT AAAATTTAG                          1979
```

FIG.4(A)

```
                            48                      1                69                79           2
MCP-1RA (CCR2-A)   MLSTSRSRFIRNTNESGEEVTTFFDYDYG--APCHKFDVKQIGAQLLPPL    48
MIP-1α/RANTESR     M----------ETPNTTEDYDTTTEFDYGDATPCQKVNERAFGAQLLPPL    40
HUMSTSR            MEGIS----IYTSDNYTEEMGS-GDYDSMK-EPCFREENANFNKIFLPTI    44
IL-8RA             MSNITDPQ-MWDFDDLNFTGMPPADEDY---SPC-MLETETLNKYVVIIA    45
IL-8RB             MESDSFEDFWKGEDLSNYSYSSTLPPFLLDAAPC-EPESLEINKYFVVII    49

MCP-1RA (CCR2-A)   YSLVFIFGFVGNMLVVLILINCKKLKCLTDIYLLNLAISDLLFLITLPLW    98
MIP-1α/RANTESR     YSLVFVIGLVGNILVVLVLVQYKRLKNMTSIYLLNLAISDLLFLFTLPFW    90
HUMSTSR            YSIIFLTGIVGNGLVILVMGYQKKLRSMTDKYRLHLSVADLLFVITLPFW    94
IL-8RA             YALVFLLSLLGNSLVMLVILYSRVGRSVTDVYLLNLALADLLFALTLPIW    95
IL-8RB             YALVFLLSLLGNSLVMLVILYSRVGRSVTDVYLLNLALADLLFALTLPIW    99

101               115       3        136
MCP-1RA (CCR2-A)   AH-SAANEWVFGNAMCKLFTGLYHIGYFGGIFFIILLTIDRYLAIVHAVF   147
MIP-1α/RANTESR     IDYKLKDDWVFGDAMCKILSGFYYTGLYSEIFFIILLTIDRYLAIVHAVF   140
HUMSTSR            AV-DAVANWYFGNFLCKAVHVIYTVNLYSSVLILAFISLDRYLAIVHATN   143
IL-8RA             AA-SKVNGWIFGTFLCKVVSLLKEVNFYSGILLLACISVDRYLAIVHATR   144
IL-8RB             AA-SKVNGWIFGTFLCKVVSLLKEVNFYSGILLLACISVDRYLAIVHATR   148

154        4          178
MCP-1RA (CCR2-A)   ALKARTVTFGVVTSVITWLVAVFASVPGIIFTKCQKEDSVYVCGPYFP--   195
MIP-1α/RANTESR     ALRARTVTFGVITSIIIWALAILASMPGLYFSKTQWEFTHHTCSLHFPHE   190
HUMSTSR            SQRPRKLLAEKVVYVGVWIPALLLTIPDFIFANVSEADDRYICDRFYPN-   192
IL-8RA             TLTQKR-HLVKFVCLGCWGLSMNLSLPFFLFRQAYHPNNSSPVCYEVLGN   193
IL-8RB             TLTQKRYLVKFI-CLSIWGLSLLLALPVLLFRRTVYSSNVSPACYEDMGN   197

204            5          231
MCP-1RA (CCR2-A)   --RGWNNFHTIMRNILGLVLPLLIMVICYSGILKTLLRCRNEKKRHRAVR   243
MIP-1α/RANTESR     SLREWKLFQALKLNLFGLVLPLLVMIICYTGIIKILLRRPNEKKS-KAVR   239
HUMSTSR            --DLWVVVFQFQHIMVGLILPGIVILFCYCIIISKLSHSKGHQKR-KALK   239
IL-8RA             DTAKWRMVLRILPHTFGFIVPLFVMLFCYGFTLRTLFKAHMGQK-HRAMR   242
IL-8RB             NTANWRMLLRILPQSFGFIVPLLIMLFCYGFTLRTLFKAHMGQ-KHRAMR   246

244      6         268
MCP-1RA (CCR2-A)   VIFTIMIVYFLFWTPYNIVILLNTFQEF-FGLSNCESTSQLDQATQVTET   292
MIP-1α/RANTESR     LIFVIMIIFFLFWTPYNLTILISVFQDF-LFTHECEQSRHLDLAVQVTEV   288
HUMSTSR            TTVILILAFFACWLPYYIGISIDSFILLEIIKQGCEFENTVHKWISITEA   289
IL-8RA             VIFAVVLIFLLCWLPYNLVLLADTLMRTQVIQETCERRNNIGRALDATEI   292
IL-8RB             VIFAVVLIFLLCWLPYNLVLLADTLMRTQVIQETCERRNHIDRALDATEI   296
```

FIG. 4(B)

```
                    295       7    313
                    ─────────────*
MCP-1RA (CCR2-A)   LGMTHCCINPIIYAFVGEKFRSLFHIALGCRIAPLQKPVCGGPGVRPGKN   342
MIP-1α/RANTESR     IAYTHCCVNPVIYAFVGERFRKYLRQLFHRRVA----------VHLVKW    327
HUMSTSR            LAFFHCCLNPILYAFLGAKFKTSAQHALTS--------------VSRGSS   325
IL-8RA             LGFLHSCLNPIIYAFIGQNFRHGFLKILA---------------MHGLVS   327
IL-8RB             LGILHSCLNPLIYAFIGQKFRHGLLKILAIH-------------GLIS    331

MCP-1RA (CCR2-A)   VKVTTQGLLDGRGKGKSIGRAPEASLQDKEGA    374
MIP-1α/RANTESR     LPFLSVDRLE-RVSSTS-PSTGEHEL--SAGF    355
HUMSTSR            LKILSKGK---RGGHSSVSTESESSS--FHSS    352
IL-8RA             KEFLARH----RVTSYT-SSSVNVS----SNL    350
IL-8RB             KDSLPKDS---RPSFVG-SSSGHTS----TTL    355
```

RECOMBINANT MAMMALIAN MONOCYTE CHEMOTACTIC PROTEIN-1 (MCP-1) RECEPTORS (MCP-1R, CCR-2)

CROSS REFERENCE TO RELATED APPLICATIONS

This application is the U.S. National Stage of PCT/US95/00476, filed Jan. 11, 1995, which is a continuation-in-part of U.S. application Ser. No. 08/182,962, filed Jan. 13, 1994, now abandoned.

This invention was made with Government support under Grant Nos. RO1-HL42662 and RO1-HL43322 awarded by the National Institutes of Health. The Government has certain rights in this invention.

This invention relates to novel cytokine receptors that mediate the chemotaxis and activation of monocytes, to the DNA sequences encoding the receptors and to processes for obtaining the receptors and producing them by recombinant genetic engineering techniques. The novel receptors appear to arise via alternative splicing of the DNA sequences.

BACKGROUND OF THE INVENTION

A growing family of regulatory proteins that deliver signals between cells of the immune system has been identified. Called cytokines, these proteins have been found to control the growth and development, and bioactivities, of cells of the hematopoietic and immune systems. Cytokines exhibit a wide range of biological activities with target cells from bone marrow, peripheral blood, fetal liver, and other lymphoid or hematopoietic organs. Exemplary members of the family include the colony-stimulating factors (GM-CSF, M-CSF, G-CSF, interleukin-3), the interleukins (IL-1, IL-2, IL-11), the interferons (alpha, beta and gamma), the tumor necrosis factors (alpha and beta) and erythropoietin.

Within this family of proteins, an emerging group of chemotactic cytokines, also called chemokines or intercrines, has been identified. These chemokines are basic, heparin-binding proteins that have proinflammatory and reparative activities. They are distinguished from other cytokines having proinflammatory and reparative activities (such as IL-1 and platelet-derived growth factor) by their characteristic conserved single open reading frames, typical signal sequences in the N-terminal region, AT rich sequences in their C-terminal untranslated regions, and rapidly inducible mRNA expression. See, e.g., Wolpe, *FASEB J.* 3:2565–73(1989) and Oppenheim, *Ann. Rev. Immunol.* 9:617–48(1991). Typically, the chemokines range in molecular mass from 8–10 kD; in humans, they are the products of distinct genes clustered on chromosomes 4 and 17. All chemokines have four cysteine residues, forming two disulfide bridges.

Two subfamilies of chemokines have been recognized, based on chromosomal location and the arrangement of the cysteine residues. The human genes for the α, or C-X-C, subfamily members are located on human chromosome 4. In this subfamily the first two cysteines are separated by one amino acid. The members of this subfamily, the human proteins IL-8 (interleukin-8), beta TG (beta thromboglobulin), PF-4 (platelet factor 4), IP-10, GRO (growth stimulating factor, also known as MGSF, melanoma grow stimulating factor) and murine MIP-2 (macrophage inhibitory protein-2), besides having the C-X-C arrangement of their first two cystein residues, exhibit homology in their amino acid sequences in the range of 30–50%.

In the beta subfamily, the first two cysteine residues are located adjacent to each other, a C-C arrangement. The human genes encoding the β subfamily proteins are located on chromosome 17 (their mouse counterparts are clustered on mouse chromosome 11 which is the counterpart of human chromosome 17). Homology in the beta subfamily ranges from 28–45% intraspecies, from 25–55% interspecies. Exemplary members include the human proteins MCP-1 (monocyte chemoattractant protein-1), LD-78 α and β, ACT-2 and RANTES and the murine proteins JE factor (the murine homologue of MCP-1), MIP-1α and β (macrophage inhibitory protein-1) and TCA-3. Human MCP-1 and murine JE factor exert several effects specifically on monocytes. Both proteins are potent chemoattractants for human monocytes in vitro and can stimulate an increase in cytosolic free calcium and the respiratory burst in monocytes. MCP-1 has been reported to activate monocyte-mediated tumoristatic activity, as well as to induce tumoricidal activity. See, e.g., Rollins, *Mol. and Cell. Biol.* 11:3125–31(1991) and Walter, *Int. J. Cancer* 49:431–35(1991). MCP-1 has been implicated as an important factor in mediating monocytic infiltration of tissues inflammatory processes such as rheumatoid arthritis and alveolitis. See, e.g., Koch, *J. Clin. Invest.* 90:772–79(1992) and Jones, *J. Immunol.* 149:2147–54(1992). The factor may also play a fundamental role in the recruitment of monocyte-macrophages into developing atherosclerotic lesions, See e.g., Nelken, *J. Clin. Invest.* 88:1121–27(1991), Yla-Herttuala, *Proc. Nat'l. Acad. Sci. USA* 88:5252–56(1991) and Cushing, *Proc. Natl. Acad. Sci. USA* 87:5134–38(1990).

Many of these chemokines has been molecularly cloned, heterologously expressed and purified to homogeneity. Several have had their receptors cloned. Two highly homologous receptors for the C-X-C chemokine IL-8 have been cloned and were shown to belong to the superfamily of G protein-linked receptors containing seven transmembrane-spanning domains. See Holmes, *Science* 253:1278–80 (1991) and Murphy, *Science* 253:1280–83(1991). More recently, a receptor for the C-C chemokines MIP-1α and RANTES has been molecularly cloned and shown to belong to the same seven transmembrane-spanning receptor superfamily. See Gao, *J. Exp. Med.* 177:1421–27(1993) and Neote, *Cell* 72:415–25(1993). This receptor, which is believed to be involved with leukocyte activation and chemotaxis, exhibits varying affinity and signaling efficacy depending on the ligand. It binds with the highest affinity and the best signaling efficacy to human MIP-1α. To MCP-1, the receptor exhibits high binding affinity relative to RANTES and huMIP-1β but transmits signal with lower efficacy. See Neote, Id., at 421–22. Although pharmacology studies predicted the existence of a specific MCP-1 receptor, and the chemokine receptors already cloned could not account for the robust responses of monocytes to MCP-1, to date no specific receptor for MCP-1 has been reported. See Wang, *J. Exp. Med.* 177:699–705(1993) and Van Riper, *J. Exp. Med.* 177:851–856(1993). The difficulty may arise at least in part from the fact that in the chemokine family individual receptors may or may not bind multiple ligands, making functional sorting, tracking and identification impractical. It has also been speculated that the receptor members of the family may not share structural features—to account for why the MCP-1 receptor has to date eluded researchers. See Edgington, *Bio/Technology II*:676–81 (1993).

There remains a need in the art for additional receptors to these chemokines. There also remains a need in the art for receptors specific for each of the C-C proteins, especially a receptor specific to MCP-1. Without a specific receptor to MCP-1, there is no practical way to develop assays of MCP-1 binding to its receptor. The availability of such assays provides a powerful tool for the discovery of antagonists of the MCP-1/MCP-1 receptor interaction. Such antagonists would be excellent candidates for therapeutics for the treatment of atherosclerosis in tumor growth suppression and in other diseases characterized by monocytic infiltrates such as rheumatoid arthritis and alvcolitis.

SUMMARY OF THE INVENTION

In one aspect the invention provides novel human chemokine receptor proteins MCP-1RA and MCP-1RB, which are substantially free from other mammalian proteins with which they are typically found in their native state. MCP-1RA and MCP-1RB are identical in amino acid sequence (SEQ ID NO:2 and SEQ ID NO:4) from the 5' untranslated region through the putative seventh transmembrane domain, but they have different cytoplasmic tails. Hence they appear to represent alternatively spliced version of the MCP-1 gene. The proteins may be produced by recombinant genetic engineering techniques. They may additionally be purified from cellular sources producing the factor constituitively or upon induction with other factors. They may also be synthesized by chemical techniques. One skilled in the art could apply a combination of the above-identified methodologies to synthesize the factor.

Active mature MCP-1RA is an approximately 374 amino acid protein having a predicted molecular weight for the mature protein of about 42,000 daltons. Its alternatively spliced version, MCP-1RB, is an approximately 360 amino acid protein having a molecular weight of about 41,000 daltons. The MCP-1R proteins of this invention display high specificity for MCP-1 when expressed in Xenopus oocytes.

Another aspect of this invention is DNA sequences (SEQ ED NO:1 and SEQ ID NO:3) that encode the expression of the MCP-1RA and 1RB proteins. These DNA sequences may include an isolated DNA sequence that encodes the expression of a MCP-1R protein as described above. As used here, "isolated" means substantially free from other mammalian DNA or protein sequences with which the subject DNA or protein sequence is typically found in its native, i.e., endogenous, state. The DNA sequences coding for active MCP-1RA and 1RB are characterized as comprising the same or substantially the same nucleotide sequence as in FIGS. 1 and 2 (SEQ ID NOS: 1 and 3), respectively, or active fragments thereof. The DNA sequences may include 5' and 3' non-coding sequences flanking the coding sequence. The DNA sequences may also encode an amino terminal signal peptide. FIGS. 1 and 2 illustrate the non-coding 5' and 3' flanking sequences and a signal sequence of the MCP-1RA and 1RB sequences, respectively, isolated from the human monocytic cell line MonoMac 6 and expressed in Xenopus oocytes.

It is understood that the DNA sequences of this invention may exclude some or all of these signal and/or flanking sequences. In addition, the DNA sequences of the present invention encoding a biologically active human MCP-1R protein may also comprise DNA capable of hybridizing under appropriate stringency conditions, or which would be capable of hybridizing under such conditions but for the degeneracy of the genetic code, to an isolated DNA sequence of FIG. 1 or FIG. 2 (SEQ ID NOS:1 and 3). Accordingly, the DNA sequences of this invention may contain modifications in the non-coding sequences, signal sequences or coding sequences, based on allelic variation, species variation or deliberate modification. Additionally, analogs of MCP-1R are provided and include truncated polypeptides, e.g., mutants in which there are variations in the amino acid sequence that retain biological activity, as defined below, and preferably have a homology of at least 80%, more preferably 90%, and most preferably 95%, with the corresponding region of the MCP-1R sequences of FIG. 1 or FIG. 2 (SEQ ID NOS: 2 and 4). Examples include polypeptides with minor amino acid variations from the native amino acid sequences of MCP-1R of FIGS. 1 and 2 (SEQ ID NOS: 2 and 4); in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on activity or functionality.

Using the sequences of FIG. 1 and FIG. 2 (SEQ ID NOS: 1, 2, 3 and 4) as well as the denoted characteristics of a MCP-1R receptor molecule in general, it is within the skill in the art to obtain other polypeptides or other DNA sequences encoding MCP-1R. For example, the structural gene can be manipulated by varying individual nucleotides, while retaining the correct amino acid(s), or varying the nucleotides, so as to modify the amino acids, without loss of activity. Nucleotides can be substituted, inserted, or deleted by known techniques, including, for example, in vitro mutagenesis and primer repair. The structural gene can be truncated at its 3'-terminus and/or its 5'-terminus while retaining its activity. For example, MCP-1RA and MCP-1RB as encoded in FIG. 1 and FIG. 2 (SEQ ID NOS:1 and 2; SEQ ID NOS:3 and 4) respectively, contain N-terminal regions which it may be desirable to delete. It also may be desirable to remove the region encoding the signal sequence, and/or to replace it with a heterologous sequence. It may also be desirable to ligate a portion of the MCP-1R sequences (SEQ ID NOS: 1 and 3), particularly that which includes the amino terminal domain to a heterologous coding sequence, and thus to create a fusion peptide with the receptor/ligand specificity of MCP-1RA or MCP-1RB.

In designing such modifications, it is expected that changes to nonconserved regions of the MCP-1R sequences (SEQ ID NOS: 1, 2, 3 and 4) will have relatively smaller effects on activity, whereas changes in the conserved regions, and particularly in or near the amino terminal domain are expected to produce larger effects. The comparison among the amino acid sequences of MCP-1RA and 1RB (SEQ ID NOS:2 and 4), the MIP-1α/RANTES receptor (SEQ ID NO:5), the orphan receptor HUMSTSR (SEQ ID NO:6) and the two IL-8 receptors (SEQ ID NOS: 7 and 8), as illustrated in FIG. 4, provides guidance on amino acid substitutions that are compatible with receptor activity. Amino acid residues that are conserved among the MCP-1R sequences (SEQ ID NOS: 2 and 4) and at least two of the other sequences (SEQ ID NOS:5, 6, 7 and 8) are not expected to be candidates for substitution. A residue which shows conservative variations among the MCP-1R sequences and at least two of the other sequences is expected to be capable of similar conservative substitution of the MCP-1R sequences. Similarly, a residue which varies non-conservatively among the MCP-1R sequences and at least three of the other sequences is expected to be capable of either conservative or nonconservative substitution. When designing substitutions to the MCP-1R sequences, replacement by an amino acid which is found in the comparable aligned position of one of the other sequences is especially preferred.

The practice of the present invention will employ, unless otherwise indicated, conventional techniques of molecular biology, microbiology, recombinant DNA, and immunology, which are within the skill of the art. Such techniques are explained fully in the literature. See, e.g., Sambrook, *Molecular Cloning: A Laboratory Manual*, Second Edition (1989); *DNA Cloning*, Volumes I and II (D. N. Glover, Ed. 1985); *Oligonucleotide Synthesis* (M. J. Gait, Ed. 1984); *Nucleic Acid Hybridization* (B. D. Hames and S. J. Higgins, Eds. 1984); *Transcription and Translation* (B. D. Hames and S. J. Higgins, Eds. 1984); *Animal Cell Culture* (R. I. Freshney, Ed. 1986); *Immobilized Cells and Enzymes* (IRL Press, 1986); B. Perbal, *A Practical Guide to Molecular Cloning* (1984); the series, *Methods in Enzymology* (Academic Press, Inc.); *Gene Transfer Vectors for Mammalian Cells* (J. H. Miller and M. P. Calos, Eds. 1987, Cold Spring Harbor Laboratory), *Methods in Enzymology*, Volumes 154 and 155 (Wu and Grossman, and Wu, Eds., respectively), (Mayer and Walker, Eds.) (1987); *Immunochemical Methods in Cell and Molecular Biology* (Academic Press, London), Scopes, (1987); *Protein Purification: Principles and Practice*, Second Edition (Springer-Verlag, N.Y.); and *Handbook of Experimental Immunology*, Volumes I–IV (D. M. Weir and C. C. Blackwell, Eds 1986). All patents, patent applications, and publications mentioned herein, both supra and infra, are hereby incorporated by reference.

Additionally provided by this invention is a recombinant DNA vector comprising vector DNA and a DNA sequence (SEQ ID NOS: 1 and 3) encoding a mammalian MCP-1R polypeptide. The vector provides the MCP-1R DNA in operative association with a regulatory sequence capable of directing the replication and expression of an MCP-1R protein in a selected host cell. Host cells transformed with such vectors for use in expressing recombinant MCP-1R proteins are also provided by this invention. Also provided is a novel process for producing recombinant MCP-1R proteins or active fragments thereof. In this process, a host cell line transformed with a vector as described above containing a DNA sequence (SEQ ID NOS: 1 and 3) encoding expression of an MCP-1R protein in operative association with a suitable regulatory sequence capable of directing replication and controlling expression of an MCP-1R protein is cultured under appropriate conditions permitting expression of the recombinant DNA. The expressed protein is then harvested from the host cell or culture medium using suitable conventional means. This novel process may employ various known cells as host cell lines for expression of the protein. Currently preferred cell lines are mammalian cell lines and bacterial cell lines.

This invention also provides compositions for use in therapy, diagnosis, assay of MCP-1R, or in raising antibodies to MCP-1R, comprising effective amounts of MCP-1R proteins prepared according to the foregoing processes. Another aspect of this invention provides an assay to assess MCP-1 binding, useful in screening for specific antagonists of the MCP-1 receptor. Such assay comprises the steps of expression and isolation of the recombinant MCP-1 receptor (s) and/or their extracellular domains and the development of a solid-phase assay for MCP-1 binding. The availability of such assays, not heretofore available, permits the development of therapeutic antagonists, useful in the treatment of atherosclerosis and other diseases characterized by monocytic infiltrates.

A further aspect of the invention therefore are pharmaceutical compositions containing a therapeutically effective amount of an MCP-1 antagonist identified using the assays of this invention. Such MCP-1 antagonist compositions may be employed in therapies for atherosclerosis, cancer and other diseases characterized by monocytic infiltrates. An additional aspect therefore, the invention includes a method for treating these and/or other diseases and pathological states by administering to a patient a therapeutically effective amount of MCP-1 antagonist, or an active fragment thereof, in a suitable pharmaceutical carrier.

Other aspects and advantages of this invention are described in the following detailed description.

BRIEF DESCRIPTION OF THE DRAWINGS

FIGS. 1A–1D illustrate the human cDNA and amino acid sequences (SEQ ID NO:1 and SEQ ID NO:2, respectively) of the isolated MCP-1 receptor clone, MCP-1RA.

FIGS. 2A–2C illustrate the human cDNA and amino acid sequences (SEQ ID NO:3 and SEQ ID NO:4, respectively) of the isolated MCP-1 receptor clone, MCP-1RB.

FIGS. 3A and 3B illustrate the results of Northern blot analysis of hematopoietic cell lines that were probed for MCP-1RA and MCP-1RB mRNA, respectively.

FIGS. 4A and 4B illustrate the predicted amino acid sequence of the MCP-1 receptor A (MCP-1RA) (SEQ ID NO:2), aligned with the MIP-1$\alpha$/RANTES receptor sequence (SEQ ID NO:5), the orphan receptor sequence HUMSTSR (SEQ ID NO:6) and the two IL-8 receptor seqeunces (SEQ ID NOS:7 and 8). Identical residues are boxed. The seven putative transmembrane domains are indicated by the horizontal bars. Gaps inserted to optimize the alignments are indicated by dashes. Amino acid numbers for each sequence are located to the right of the sequences.

FIG. 5 graphically depicts the functional expression of MCP-1R protein in Xenopus oocytes as assayed by measuring calcium mobilization in the presence of MCP-1.

FIG. 6 graphically depicts the results of the calcium efflux assay used to confirm gene expression and responsiveness to MCP-1 as described in Example 4.

FIGS. 7A and 7B graphically depict the binding of $^{125}$I-MCP-1 to the recombinant MCP-1RB receptor, as described in detail in Example 5.

FIGS. 8A–8C graphically depict the results of the MCP-1RB receptor-mediated calcium mobilization experiments also described in detail in Example 5. FIG. 8A depicts intracellular calcium flux as a function of MCP-1 concentration (nM). Calcium transients peaked at 4–8 sec. after addition of MCP-1 and returned to baseline within 90 sec. of activation. FIG. 8B depicts the MCP-1 stimulated calcium mobilization ($EC_{50}$=3.4 nM) and the lack of stimulated calcium mobilization by other cytokines. FIG. 8C illustrates that MCP-1 desensitized the cells to a second addition of MCP-1.

DETAILED DESCRIPTION

I. Introduction

This invention provides biologically active human chemokine receptors, MCP-1RA and 1RB, substantially free from association with other mammalian proteins and proteinaceous material with which they are normally associated in its native state. MCP-1R proteins can be produced by recombinant techniques to enable production in large quantities useful for assaying potential antagonists to identify candidates for therapeutics for the treatment of atherosclerosis and other monocytic associated diseases such as cancer and rheumatoid arthritis. Alternatively, MCP-1R proteins may be obtained as a homogeneous protein purified from a mammalian cell line secreting or expressing it, or they may be chemically synthesized.

Human MCP-1RA was isolated from a derivative of a human monocytic leukemia cell line, MonoMac 6 (MM6). Because monocytes are difficult to isolate in large quantities and express less than 2000 high-affinity binding sites per cell, a cell line that responded well to MCP-1 was needed. Because of their consistency in response, the MM6 cell line was chosen. It can be obtained from the DSM German Collection of Microorganisms and Cell Cultures (Mascheroder Weg1b, 3300 Braunschweig, Germany); see also, Ziegler-Heitbrock, *Int. J. Cancer* 41:456(1988). Cells were grown in appropriate medium and then tested for changes in intracellular calcium in response to MCP-1 and other chemokines. A cDNA library was prepared from MonoMac 6 mRNA according to methods previously described. See Vu, *Cell* 64:1057–68(1991). A polymerase chain reaction (PCR)-based strategy using degenerate oligonucleotide primers corresponding to conserved sequences in the second and third transmembrane domains of the other chemokine receptors and in the HUMSTSR orphan receptor was employed (See SEQ ID NOS: 5, 6, 7 and 8). Amplification of cDNA derived from MM6 cells using the primers yielded a number of PCR products corresponding in size to those expected for a seven-transmembrane receptor. Analysis of the subcloned PCR products revealed cDNAs encoding the predicted arrangements of the receptors upon which the primers were designs, along with one cDNA that appeared to encode a novel receptor.

To obtain a full-length version of this clone, an MM6 cDNA library was constructed and probed with the PCR product. An isolated clone of 2.1 kb was obtained and called MCP-1RA. FIGS. 1A–1D illustrate the cDNA sequence (SEQ ID NO: 1) and the predicted amino acid sequence (SEQ ID NO:2) of the clone. The nucleotide sequence (SEQ ID NO:1) comprises 2232 base pairs, including a 5' noncoding sequence of 39 base pairs and a 3' noncoding sequence of 1071 base pairs. The MCP-1RA sequence is characterized by a single long open reading frame encoding a 374 amino acid following the initiation methionine at position 23.

The nucleotide sequence of MCP-1RA cDNA (SEQ ID NO: 1) was compared with the nucleotide sequences recorded in Genbank. Homology was found with the coding sequences of the receptors for MIP-1 alpha/RANTES, the HUMSTSR orphan receptor and IL-8 (SEQ ID NOS: 5, 6, 7 and 8, respectively). No significant homology was found between the coding sequence of MCP-1RA and any other published polypeptide sequence.

The predicted amino acid sequence of MCP-1RA (SEQ ID NO:2) reveals seven putative transmembrane domains and an extracellular amino terminus of 40 residues. Further analysis of the MCP-1RA amino acid sequence reveals several interesting features. Despite its homology with the related MIP-1 alpha/RANTES receptor and the IL-8 receptors, MCP-1RA exhibits significant divergence in its amino and carboxyl termini. See FIGS. 4A–4B (SEQ ID NOS: 2, 5, 6, 7 and 8). Additionally, a striking identity between MCP-1RA and the MIP-1 alpha/RANTES receptor occurs in a 31 amino acid sequence beginning with the septate IFFIILL at the end of the third transmembrane domain.

Preliminary biological characterization indicates that MCP-1RA confers robust and remarkable specific responses to nanomolar concentrations of MCP-1. Surprisingly, no response was elicited by the MIP-1α, MIP-1β, RANTES or Il-8, even at concentrations of 500 nanomoles.

Analysis of additional clones in the MM6 cDNA library revealed a second sequence, identical to the MCP-1RA sequence from the 5' untranslated region through the putative seventh transmembrane domain but containing a different cytoplasmic tail. This second sequence (SEQ ID NOS:3 and 4), termed MCP-1RB, appears to be an alternatively spliced version of MCP-1RA. It is further characterized below.

The MCP-1R polypeptides provided herein also include polypeptides encoded by sequences similar to that of MCP-1RA and 1RB (SEQ ID NOS: 1, 2, 3 and 4) in FIGS. 1A–1D and 2A–2C, but into which modifications are naturally provided or deliberately engineered. This invention also encompasses such novel DNA sequences, which code on expression for MCP-1R polypeptides having specificity for the MCP-1 receptor. These DNA sequences include sequences substantially the same as the DNA sequences (SEQ ID NOS: 1 and 3) of FIGS. 1A–1D and 2A–2C and biologically active fragments thereof, and such sequences that hybridize under stringent hybridization conditions to the DNA sequences (SEQ ID NOS: 1 and 3) of FIGS. 1A–1D and 2A–2C. See Maniatis, *Molecular Cloning (A Laboratory Manual)*, Cold Spring Harbor Laboratory (1982), pages 387–389. One example of such stringent conditions is hybridization at 4 ×SSC, at 65 degrees C., followed by a washing in 0.1×SSC at 65 degrees C. for one hour. Another exemplary stringent hybridization scheme uses 50% formamide, 4×SSC at 42 degrees C.

DNA sequences that code for MCP-1R polypeptides but differ in codon sequence due to the degeneracies inherent in the genetic code are also encompassed by this invention. Allelic variations, i.e., naturally occurring interspecies base changes that may or may not result in amino acid changes, in the MCP-1R DNA sequences (SEQ ID NOS: 1 and 3) of FIGS. 1A–1D and 2A–2C encoding MCP-1R polypeptides having MCP-1R activity (for example, specificity for the MCP-1 receptor) are also included in this invention.

II. Modes for Carrying Out the Invention

Methods for producing a desired mature polypeptide can include the following techniques. First, a vector coding for a MCP-1R polypeptide can be inserted into a host cell, and the host cell can be cultured under suitable culture conditions permitting production of the polypeptide.

The MCP-1R genes or fragments thereof can be expressed in a mammalian, insect, or microorganism host. The polynucleotides encoding MCP-1R genes are inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes.

A suitable expression vector is one that is compatible with the desired function (e.g., transient expression, long term expression, integration, replication, amplification) and in which the control elements are compatible with the host cell.

A. Expression in mammalian cells

Vectors suitable for replication in mammalian cells are known in the art, and can include viral replicons, or sequences that ensure integration of the sequence encoding MCP-1R into the host genome. Exemplary vectors include those derived from simian virus SV40, retroviruses, bovine papilloma virus, vaccinia virus, and adenovirus.

As is known in the art, the heterologous DNA, in this case MCP-1R DNA, is inserted into the viral genome using, for example, homologous recombination techniques. The insertion is generally made into a gene which is non-essential in nature, for example, the thymidine kinase gene (tk), which also provides a selectable marker. Plasmid shuttle vectors that greatly facilitate the construction of recombinant viruses have been described (see, for example, Mackett, et al. (1984); Chakrabarti, et al. (1985); Moss (1987)). Expression of the heterologous polypeptide then occurs in cells or individuals which are immunized with the live recombinant virus.

Such suitable mammalian expression vectors usually contain a promoter to mediate transcription of foreign DNA sequences and, optionally, an enhancer. Suitable promoters for mammalian cells are known in the art and include viral prompters such as that from simian virus 40 (SV40), cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See Maniatis, *Science* 236:1237(1987), Alberts, *Molecular Biology of the Cell*, 2nd Ed. (1989). Enhancer elements derived from viruses may be particularly useful, because they typically have a broader host range. Examples useful in mammalian cells include the SV40 early gene enhancer (see Dijkema, *EMBO J.* 4:761(1985)) and the enhancer/promoters derived from the long terminal repeat (LTR) of the RSV (see Gorman, *Proc. Natl. Acad. Sci.* 79:6777(1982b)) and from human cytomegalovirus (see Boshart, *Cell* 41:521(1985)). Additionally, some enhancers are regulatable and become active only in the presence of an inducer, such as a hormone or metal ion (see Sassone-Corsi and Borelli, *Trends Genet.* 2:215(1986)); Maniatis, *Science* 236:1237(1987)).

In addition, the expression vector can and will typically also include a termination sequence and poly(A) addition sequences which are operably linked to the MCP-1R coding sequence.

Sequences that cause amplification of the gene may also be desirably included in the expression vector or in another vector that is co-translated with the expression vector containing an MCP-1R DNA sequence, as are sequences which encode selectable markers. Selectable markers for mammalian cells are known in the art, and include for example, thymidine kinase, dihydrofolate reductase (together with methotraxate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes an MCP-1R polypeptide can be used for transformation of a suitable mammalian host cell.

Transformation can be by any known method for introducing polynucleotides into a host cell, including, for example packaging the polynucleotide in a virus and transducing a host cell with the virus. The transformation procedure used depends upon the host to be transformed. Methods for introduction of heterologous polynucleotides into mammalian cells are known in the art and include dextran-mediated transection, calcium phosphate precipitation, polybrene mediated transection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

B. Expression in Insect Cells

In the case of expression in insect cells, generally the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

Exemplary transfer vectors for introducing foreign genes into insect cells include pAc373 and pVL985. See Luckow and Summers, *Virology* 17:31(1989).

The plasmid usually also contains the polyhedron polyadenylation signal and a procaryotic ampicillin-resistance (amp) gene and origin of replication for selection and propagation in *E. coli*. See Miller, *Ann. Rev. Microbiol.* 42:177(1988).

Baculovirus transfer vectors usually contain a baculovirus promoter, i.e., a DNA sequence capable of binding a baculovirus RNA polymerase and initiating the downstream (5' to 3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector can also have an enhancer, which, if present, is usually distal to the structural gene. Expression can be either regulated or constitutive.

C. Expression in Microorganisms—Yeast and Bacteria

Fungal expression systems can utilize both yeast and filamentous fungi hosts. Examples of filamentous fungi expression systems are Aspergillus, as described in EP Patent Pub. No. 357 127 (published Mar. 7, 1990), and *Acremonium Chrysogenum*, described in EP Patent Pub. No. 376 266 (published Jul. 4, 1990).

A yeast expression system can typically include one or more of the following: a promoter sequence, fusion partner sequence, leader sequence, transcription termination sequence.

A yeast promoter, capable of binding yeast RNA polymerase and initiating the downstream (3') transcription of a coding sequence (e.g. structural gene) into mRNA, will have a transcription initiation region usually placed proximal to the 5' end of the coding sequence. This transcription initiation region typically includes an RNA polymerase binding site (a "TATA Box") and a transcription initiation site. The yeast promoter can also have an upstream activator sequence, usually distal to the structural gene. The activator sequence permits inducible expression of the desired heterologous DNA sequence. Constitutive expression occurs in the absence of an activator sequence. Regulated expression can be either positive or negative, thereby either enhancing or reducing transcription.

Particularly useful yeast promoter sequences include alcohol dehydrogenase (ADH) (EP Patent Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)(EP Patent Pub. No. 329 203). The yeast PHO5 gene, encoding acid phosphatase, also provides useful promoter sequences. See Myanohara, *Proc. Natl. Acad. Sci. USA* 80:1(1983).

An MCP-1R gene or an active fragment thereof can be expressed intracellularly in yeast. A promoter sequence can be directly linked with an MCP-1R gene or fragment, in which case the first amino acid at the N-terminus of the recombinant protein will always be a methionine, which is encoded by the ATG start codon. If desired, methionine at the N-terminus can be cleaved from the protein by in vitro incubation with cyanogen bromide.

Intracellularly expressed fusion proteins provide an alternative to direct expression of an MCP-1R sequence. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of an MCP-1R sequence and expressed in yeast. The DNA sequence at the junction of the two amino acid sequences may or may not encode a cleavable site. See, e.g., EP Patent Pub. No. 196 056. Alternatively, MCP-1R polypeptides can also be secreted from the cell into the growth media by creating a fusion protein comprised of a leader sequence fragment that provides for secretion in yeast or bacteria of the MCP-1R polypeptides. Preferably, there are processing sites encoded between the leader fragment and the MCP-1R sequence (SEQ ID NOS: 1 and 3) that can be cleaved either in vivo or in vitro. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (EP Patent Pub. No. 12 873) and the A-factor gene (U.S. Pat. No. 4,588,684). Alternatively, leaders of non-yeast origin, such as an interferon leader, can be used to provide for secretion in yeast (EP Patent Pub. No. 60057). Transcription termination sequences recognized by yeast are regulatory regions located 3' to the translation stop codon. Together with the promoter they flank the desired heterologous coding sequence. These flanking sequences direct the transcription of an mRNA which can be translated into the MCP-1R polypeptide encoded by the MCP-1R DNA.

Typically, the above described components, comprising a promoter, leader (if desired), coding sequence of interest, and transcription termination sequence, are put together in plasmids capable of stable maintenance in a host, such as yeast or bacteria. The plasmid can have two replication systems, so it can be maintained as a shuttle vector, for example, in yeast for expression and in a procaryotic host for cloning and amplification. Examples of such yeast-bacteria shuttle vectors include YEp24 (see Botstein, *Gene* 8:17–24 (1979)), pCl/1 (see Brake, *Proc. Natl. Acad. Sci. USA* 81:4642–4646(1984)), and YRp17 (see Stinchcomb, *J. Mol. Biol.* 158:157(1982)). In addition, the plasmid can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the MCP-1R polypeptides. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. See Orr-Weaver, *Methods In Enzymol.* 101:228–245(1983) and Rine, *Proc. Natl. Acad. Sci. USA* 80:6750(1983).

Typically, extrachromosomal and integrating expression vectors can contain selectable markers to allow for the selection of yeast strains that have been transformed. Selectable markers can include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions. See Butt, *Microbiol. Rev.* 51:351(1987).

Alternatively, some of the above described components can be put together into transformation vectors. Transformation vectors are typically comprised of a selectable marker that is either maintained in a replicon or developed into an integrating vector, as described above.

Expression and transformation vectors, either extrachromosomal or integrating, have been developed for transformation into many yeasts. Exemplary yeasts cell lines are Candida albicans (Kurtz, *Mol. Cell. Biol.* 6:142(1986), Candida maltosa (Kunze, *J. Basic Microbiol.* 25:141(1985), Hansenula polymorpha (Gleeson, *J. Gen. Microbiol.* 132:3459(1986) and Roggenkamp, *Mol. Gen. Genet.* 202:302(1986), Kluyveromyces fragilis (Das, *J. Bacteriol.* 158:1165(1984), Kluyveromyces lactis (De Louvencourt, *J. Bacteriol.* 154:737(1983) and Van den Berg, *Bio/Technology* 8:135(1990), Pichia guillerimondii (Kunze, *J. Basic Microbiol.* 25:141(1985), Pichia pastoris (Cregg, *Mol. Cell. Biol.* 5:3376 (1985), Saccharomyces cerevisiae (Hinnen, *PROC. NATL. ACAD. SCI. USA* 75:1929(1978) and Ito, *J. Bacteriol.* 153:163(1983), Schizosaccharomyces pombe (Beach and Nurse, *Nature* 300:706(1981), and Yarrowia lipolytica (Davidow, *Curr. Genet.* 10:380471(1985) and Gaillardin, *Curr. Genet.* 10:49(1985)

Methods of introducing exogenous DNA into yeast hosts are well-known in the art, and typically include either the transformation of spheroplasts or of intact yeast cells treated with alkali cations. Transformation procedures usually vary with the yeast species to be transformed. See the publications listed in the foregoing paragraph for appropriate transformation techniques.

Additionally, the MCP-1R gene or fragment thereof can be expressed in a bacterial system. In such system, a bacterial promoter is any DNA sequence capable of binding bacterial RNA polymerase and initiating the downstream (3') transcription of a coding sequence (e.g. a desired heterologous gene) into mRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*). See Raibaud, *Ann. Rev. Genet.* 18:173(1984). Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (see Chang, *Nature* 198:1056(1977), and maltose. Additional examples include promoter sequences derived from biosynthetic enzymes such as tryptophan (trp) (see Goeddel, *NUC. ACIDS RES.* 8:4057(1981), Yelverton, *Nuc. Acids Res.* 9:731(1981), U.S. Pat. No. 4,738,921 and EP Patent Pub. Nos. 36 776 and 121 775). The β-lactamase (bla) promoter system (see Weissmann, *Interferon* 3 (ed. I. Gresser), the bacteriophage lambda PL promoter system (see Shimatake, *Nature* 292:128(128) and the T5 promoter system (U.S. Pat. No. 4,689,406) also provides useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter such as the tac promoter (see U.S. Pat. No. 4,551,433, Amann, *Gene* 25:167 (1983) and de Boer, *Proc. Natl. Acad. Sci.* 80:21(1983)). A bacterial promoter can include naturally occurring promoters of non-bacterial origin that have the ability to bind bacterial RNA polymerase and initiate transcription. A naturally occurring promoter of non-bacterial origin can be coupled with a compatible RNA polymerase to produce high levels of expression of some genes in prokaryotes. The bacteriophage T7 RNA polymerase/promoter system is exemplary. (see Studier, *J. Mol. Biol.* 189:113(1986) and Tabor, *Proc. Natl. Acad. Sci.* 82:1074(1985)).

In addition to a functioning promoter sequence, an efficient ribosome binding site is also useful for the expression of the MCP-1R gene or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon (see Shine, *Nature* 254:34(1975). The SD sequence is thought to promote binding of mRNA to the ribosome by the pairing of bases between the SD sequence and the 3' and of *E. coli* 16S rRNA (see Steitz, *Biological Regulation and Development: Gene Expression* (ed. R. F. Goldberger)(1979)).

MCP-1R protein can be expressed intracellularly. A promoter sequence can be directly linked with an MCP-1R gene or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase. See EP Patent Pub. No. 219 237.

Fusion proteins provide an alternative to direct expression. Typically, a DNA sequence encoding the N-terminal portion of an endogenous bacterial protein, or other stable protein, is fused to the 5' end of heterologous MCP-1R coding sequences. Upon expression, this construct will provide a fusion of the two amino acid sequences. For example, the bacteriophage lambda cell gene can be linked at the 5' terminus of an MCP-1R gene or fragment thereof and expressed in bacteria. The resulting fusion protein preferably retains a site for a processing enzyme (factor Xa) to cleave the bacteriophage protein from the MCP-1R gene or fragment thereof (see Nagai, *Nature* 309:810(1984). Fusion proteins can also be made with sequences from the lacZ gene (Jia, *Gene* 60:197(1987),the trpE gene (Allen, *J. Biotechnol.* 5:93(1987) and Makoff, *J. Gen. Microbiol.* 135:11(1989), and the Chey gene (EP Patent Pub. No. 324 647) genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g., ubiquitin specific processing-protease) to cleave the ubiquitin from the MCP-1R polypeptide. Through this method, mature MCP-1R polypeptides can be isolated. See Miller, *Bio/Technology* 7:698(1989).

Alternatively, MCP-1R polypeptides can also be secreted from the cell by creating chimeric DNA molecules that encode a fusion protein comprised of a signal peptide sequence fragment that provides for secretion of the MCP-1R polypeptides in bacteria. (See, for example, U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the piroplasmic specie, located between the inner and outer membrane of the cell (gram-negative bacteria). Preferably there are processing sites, which can be cleaved either in vivo or in vitro encoded between the signal peptide fragment and the MCP-1R polypeptide.

DNA encoding suitable signal sequences can be derived from genes for secreted bacterial proteins, such as the *E. coli* outer membrane protein gene (ompA) (Masui, Experimental Manipulation of Gene Expression (1983) and Ghrayeb, *EMBO J.* 3:2437(1984)) and the *E. coli* alkaline phosphatase signal sequence (phoA) (see Oka, *Proc. Natl. Acad. Sci.* 82:7212(1985). The signal sequence of the alpha-amylase gene from various Bacilus strains can be used to secrete heterologous proteins from *B. subtilis* (see Palva, *Proc. Nati. Acad. Sci.* 79:5582(1982) and EP Patent Pub. No. 244 042).

Transcription termination sequences recognized by bacteria are regulatory regions located 3' to the translation stop codon. Together with the promoter they flank the coding sequence. These sequences direct the transcription of an mRNA which can be translated into the MCP-1R polypeptide encoded by the MCP-1R DNA sequence (SEQ ID NOS:1 and 3). Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the promoter, signal sequence (if desired), coding sequence of interest, and transcription termination sequence are maintained in an extrachromosomal element (e.g., a plasmid) capable of stable maintenance in the bacterial host. The plasmid will have a replication system, thus allowing it to be maintained in the bacterial host either for expression or for cloning and amplification. In addition, the plasmid can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. See e.g., EP Patent Pub. No. 127 328.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (see Davies, *Ann. Rev. Microbiol.* 32:469(1978). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in an extrachromosal vector or an integrating vector, as described above.

Expression and transformation vectors, either extrachromosomal or integrating, have been developed for transformation into many bacteria. Exemplary are the expression vectors disclosed in Palva, *Proc. Natl. Acad. Sci.* 79:5582 (1982), EP Patent Pub. Nos. 036 259 and 063 953 and PCT Patent Publication WO 84/04541 (for *B. subtilis*); in Shimatake, *Nature* 292:128(1981), Amann, *Gene* 40:183 (1985), Studier, *J. Mol. Biol.* 189:113(1986) and EP Patent Pub. Nos. 036 776, 136 829 and 136 907 (for *E.coli*); in Powell, *Appl. Environ. Microbiol.* 54:655(1988) and U.S. Pat. No. 4,745,056 (for Streptococcus).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Exemplary methodologies can be found in Masson, *FEMS Microbiol. Let.* 60:273(1989), Palva, *Proc. Natl. Acad. Sci.* 79:5582(1982), EP Patent Pub. Nos. 036 259 and 063 953 and PCT Patent Pub. WO 84/04541 for Bacillus transformation. For campylobacter transformation, see e.g., Miller, *Proc. Natl. Acad. Sci.* 85:856(1988) and Wang, *J. Bacteriol.* 172:949(1990). For *E.coli*, see e.g., Cohen, *Proc. Natl. Acad. Sci.* 69:2110(1973), Dower, *Nuc. Acids Res.* 16:6127 (1988), Kushner, *Genetic Engineering: Proceedings of the International Symposium on Genetic Engineering* (eds. H. W. Boyer and S. Nicosia), Mandel, *J. Mol. Biol.* 53:159 (1970) and Taketo, *Biochem. Biophys. Acta* 949:318(1988). For Lactobacillus and Pseudomonas, see e.g., Chassy, *FEMS Microbiol. Let.* 44:173(1987) and Fiedler, *Anal. Biochem.* 170:38(1988), respectively. For Streptococcus, see e.g., Augustin, *FEMS Microbiol. Let.* 66:203(1990), Barany, *J. Bacteriol.* 144:698(1980), Harlander, *Streytococcal Genetics* (ed. J. Ferretti and R. Curtiss III)(1987), Perry, *Infec. Immun.* 32:1295(1981), Powell, *Appl. Environ. Microbiol.* 54:655(1988) and Somkuti, *Proc. 4th Evr. Cong. Biotechnology* 1:412(1987).

III. Expression and Detection of Expressed MCP-1R Proteins

In order to obtain MCP-1R expression, recombinant host cells derived from the transformants are incubated under conditions which allow expression of the MCP-1R encoding sequence (SEQ ID NOS:1 AND 3). These conditions will vary, depending upon the host cell selected. However, the conditions are readily ascertainable to those of ordinary skill in the art, based upon what is known in the art.

Detection of an MCP-1R protein expressed in the transformed host cell can be accomplished by several methods. For example, detection can be by enzymatic activity (or increased enzymatic activity or increased longevity of enzymatic activity) using fluorogenic substrates which are comprised of a dibasic cleavage site for which an MCP-1R protein is specific. An MCP-1R protein can also be detected by its immunological reactivity with anti-MCP-1R antibodies.

IV. Identification of MCP-1 Receptor Antagonists

Different ligands of a cellular receptor are classified on the basis of their capacity to induce biological responses. Substances that are both capable of binding to the receptor and triggering a response are classified as agonists. By contrast, ligands that are capable of binding to the receptor but are incapable of triggering a response are classified as antagonists. Antagonists compete, sometimes extremely effectively, with the natural ligand or its agonists, leading to functional receptor inactivation (receptor antagonism).

A method is provided for identifying ligands of the MCP-1 receptor, such as antagonists. The method comprises transfecting a mammalian cell line with an expression vector comprising nucleic acid sequences encoding the N-terminal domain of MCP-1 receptor (see SEQ ID NOS:1 and 3). The N-terminal domain of the MCP-1 receptor may be expressed alone or in combination with other domains of the MCP-1 receptor. The other domains may be extracellular, intracellular or transmembrane domains. Moreover, a chimaeric protein may be expressed, where the other domains are the corresponding domains from related proteins, such as those in FIG. 4 (SEQ ID NOS:5, 6, 7 and 8). The N-terminal domain may also be expressed as a portion of the native MCP-1 receptor. Expression of extracellular domains is preferred where soluble protein for solid phase assays is required.

The antagonist is identified by adding an effective amount of an organic compound to the culture medium used to propogate the cells expressing the N-terminal domain of MCP-1 receptor. An effective amount is a concentration sufficient to block the binding of MCP-1 to the receptor domain. The loss in binding of MCP-1 to the receptor may be assayed using various techniques, using intact cells or in solid-phase assays.

For example, binding assays similar to those described for IL-7 in U.S. Pat. No. 5,194,375 may be used. This type of assay would involve labelling MCP-1 and quantifying the amount of label bound by MCP-1 receptors in the presence and absence of the compound being tested. The label used may, for example, be a radiolabel, e.g. $^{125}I$ or a fluorogenic label.

Alternatively, an immunoassay may be employed to detect MCP-1 binding to its receptor by detecting the immunological reactivity of MCP-1 with anti-MCP-1 antibodies in the presence and absence of the compound being tested. The immunoassay may, for example, involve an antibody sandwich assay or an enzyme-linked immunoassay. Such methods are well known in the art and are described in *Methods in Enzymology*, Volumes 154 and 155 (Wu and Grossman, and Wu, Eds., respectively), (Mayer and Walker, Eds.) (1987); *Immunochemical Methods in Cell and Molecular Biology* (Academic Press, London).

Pharmaceutical compositions comprising the MCP-1 receptor antagonist may be used for the treatment of disease characterized by monocytic infiltrates, such as rheumatoid arthritis and alveolitis. The antagonist is administered as a pharmaceutical composition comprising a therapeutically effective amount of the antagonist and a pharmaceutically acceptable vehicle. Such pharmaceutical compositions may also contain pharmaceutically acceptable carriers, diluents, fillers, salts, buffers, stabilizers and/or other materials well-known in the art. The term "pharmaceutically acceptable" means a material that does not interfere with the effectiveness of the biological activity of the active ingredient(s) and that is not toxic to the host to which it is administered. The characteristics of the carrier or other material will depend on the route of administration.

Administration can be carried out in a variety of conventional ways. Parenteral administration is currently preferred. In such cases, the antagonist composition may be in the form of a non-pyrogenic, sterile, parenterally acceptable aqueous solution. The preparation of such parenterally acceptable solutions, having due regard to pH, isotonicity, stability and the like, is within the skill in the art. In the long term, however, oral administration will be advantageous, since it is expected that the active antagonist compositions will be used over a long time period to treat chronic conditions.

The amount of active ingredient will depend upon the severity of the condition, the route of administration, the activity of the antagonist, and ultimately will be decided by the attending physician. It is currently contemplated, however, that the various pharmaceutical compositions should contain about 10 micrograms to about 1 milligram per milliliter of antagonist.

In practicing the method of treatment of this invention, a therapeutically effective amount of the antagonist composition is administered to a human patient in need of such treatment as a result of having a condition characterized by monocytic infiltrates. The term "therapeutically effective amount" means the total amount of the active component of the method or composition that is sufficient to show a meaningful patient benefit, i.e., healing of chronic conditions or increase in rate of healing. A therapeutically effective dose of an antagonist composition of this invention is contemplated to be in the range of about 10 micrograms to about 1 milligram per milliliter per dose administered. The number of doses administered may vary, depending on the individual patient and the severity of the condition.

The invention is further described in the following examples, which are intended to illustrate the invention without limiting its scope.

V. Examples

Standard procedures for the isolation and manipulation of DNA are from Sambrook, et al. (1989). Plasmid DNA was propagated in *E. coli* strains HB101, D1210 or XL-1 Blue (Stratagene). DNA sequencing was performed by the dideoxy chain termination method (Sanger, 1977) using M13 primers as well as specific internal primers.

EXAMPLE 1

PCR Identification of cDNA Clones

To identify and clone new members of the chemokine receptor gene family, degenerate oligonucleotide primers were designed and synthesized corresponding to the conserved sequences NLAISDL (SEQ ID NO: 11) in the second and DRYLAIV (SEQ ID NO:12) in the third transmembrane domains of the MIP-1α/RANTES receptor, the IL-8 receptors and the HUMSTSR orphan receptor (GenBank Accession #M99293). Amplification of cDNA derived from MM6 cells with the primers yielded a number of PCR products corresponding in size to those expected for a seven transmembrane receptor. Analysis of the subcloned PCR products revealed cDNAs encoding the predicted fragments of the receptors from which the primers were designed as well as one cDNA that appeared to encode a novel protein. To obtain a full-length version of this clone, a MM6 cDNA library was constructed in pFROG and probed by hybridization with the PCR product. A 2.1 kb cDNA clone was obtained. Analysis of additional clones in the MM6 cDNA library revealed a second sequence that was identical to the 2.1 kb cDNA sequence first obtained from the 5' untranslated region through the putative seventh transmembrane domain but contained a different cytoplasmic tail from the 2.1 kb cDNA sequence first obtained. Two independent clones in the library were found to contain the second sequence, which appears to represent alternative splicing of the carboxyl-terminal tail of the MCP-1R protein. The two sequences are denoted MCP-1RA and MCP-1RB, monocyte chemoattractant protein-1 receptors A and B, representing, respectively, the first and second sequences isolated (SEQ ID NOS:1, 2, 3 and 4). Details of the materials and methods used follow.

1. Oligonucleotide Synthesis

Oligonucleotide adapters, probes, and primers were synthesized on an Applied Biosystems (Foster City, Calif.) instrument according to the manufacturer's instructions. The degenerate oligonucleotide primers corresponding to conserved sequences in the second and third transmembrane domains as noted above and incorporating EcoRI and XhoI restriction sites in their 5' ends that were used to identify MCP-1R were a 27-mer, 5' CGC TCG AGA CCT (G or A)(G or T)C (C or A)(A, T or G)T (T or G)(T or G)C (T or C)GA CCT 3' (SEQ ID NO:9) and a 31-mer 5' GC GAA TTC TGG AC(G or A) ATG GCC AGG TA(C,A or G) C(T or G)G TC 3' (SEQ ID NO:10).

2. Polymerase Chain Reactions (PCR)

MM6 cells, which are derived from a human monocytic leukemia (see Weber, *Eur. J. Immunol.* 23:852–59(1993)) were obtained from the DSM German Collection of Microorganisms and Cell Cultures, Masheroder Weglb, 3300 Braunschweig, Germany. The cells were grown in RPMI-1640 (GIBCO BRL, Grand Island, N.Y.), supplemented with 10% fetal calf serum, 25 mM Hepes, and antibiotics. Total RNA was isolated from the MM6 cells by the method of Chomczynski and Sacchi. See Chomczynski, *Anal. Biochem.* 162:156–59(1987). Poly A+ RNA was obtained by affinity chromatography on oligo dT cellulose columns (Pharmacia, Piscataway, N.J.). First strand cDNA synthesis was performed starting with 5 µg of MM6 poly A+ RNA according to the manufacturer's instructions (Pharmacia).

PCR reactions were carried out for 30 cycles beginning with a 1-minute incubation at 94° C., 2 minutes at 50° C., 1.5 minutes at 72° C., and a final elongation step at 72° C. for 4 minutes using the PCR primers described above (SEQ ID NOS:9 and 10) at a final concentration of 1 µM and MM6 cDNA at approximately 10 ng/ml. PCR products migrating between 200–300 base pairs on a 1.5% agarose gel were excised, subcloned into pBluescript (sk⁻) and sequenced using fluorescently labeled dideoxyribonucleotides as described by Sanger, *Proc Natl Acad SciUSA* 74:5463–67 (1977). Sequence analysis revealed cDNAs encoding the predicted fragments of the receptors upon which the primers were designed and one cDNA which appeared to encode a novel protein. To obtain a full-length version of this clone, an appropriate cell line was chosen and a cDNA library was constructed in pFROG and probed with this PCR product, as detailed in subsections 3 and 4 below.

3. Identification of the MM6 Cell Line

Because monocytes are difficult to isolate in usable quantity and express less than 2000 high affinity MCP-1 binding sites per cell, a cultured cell line that responded well to MCP-1 had to be identified. Using the calcium efflux assay as described in Vu, Cell 64:1057–68(1991), MCP-1 induced calcium fluxes in various cell lines were measured. No calcium flux was detected in undifferentiated human HL-60 cells and human erythroleukemia (HEL) cells. In contrast, a dose-dependent calcium flux was detected in MM6 cells, with half maximal stimulation at 4 nM MCP-1. The response of MM6 cells to MCP-1 could not be ablated by prior exposure to RANTES, whereas the response to RANTES was partially blocked by prior exposure to MCP-1. Similar results obtained when MIP-1α was used instead of RANTES.

4. Expression Cloning of MCP-1 Receptor

The overall strategy for cloning the MCP-1 receptor was to confer MCP-1 responsiveness to Xenopus oocytes that were microinjected with RNA encoding the receptor. This methodology has been successfully employed to clone the 5-HT, thrombin, IL8RA, and MIP-1α/RANTES receptors. Oocytes are harvested from gravid frogs, and treated with collagenase to remove the follicular cells. The cDNA library is electroporated into bacterial host cells which are then divided into pools of 5,000 to 50,000 colonies/petri dish. DNA is prepared from each pool of bacteria and linearized. One day after harvesting, the oocytes are microinjected with poly A+ RNA or cRNA transcribed from the linearized cDNAs and incubated for two days to allow protein expression. On the day of the experiment, the oocytes are loaded with $^{45}$Ca, washed to remove unincorporated $^{45}$Ca, and then incubated with potential ligands. In the presence of the appropriate ligand a significant afflux of $^{45}$Ca is detected. Uninjected oocytes are used as controls. A minimum of 1,000,000 colonies are screened (i.e., 20 to 200 pools) and if a positive pool is found it is subdivided (sibed) into smaller pools which are then individually screened. The process is repeated until a single clone is obtained.

As a prelude to undertaking this very labor intensive approach, poly A+ RNA from large scale preparations of THP-1 and MM6 cells was injected into oocytes, but failed to confer MCP-1 dependent signaling. Furthermore, larger mRNA species were enriched by size fractionation of 200–300 μg of poly A+ THP-1 and MM6 RNA on sucrose gradients before injecting individual fractions into oocytes. Once again MCP-1 dependent signaling in oocytes was not demonstrated. In addition, injection of a limited number of cRNAs transcribed from library pools also failed to confer signaling. These experiments suggested that the MCP-1 receptor message is most likely of low abundance, and not detectable in a pool size large enough to make expression cloning by sib-selection feasible. For this reason, the polymerase chain reaction (PCR)-based strategy was pursued.

5. Construction and Screening of the MM6 cDNA Library

A cDNA library was constructed in the vector pFROG, a modified version of pCDM6 that includes approximately 100 bases of 5' untranslated xenopus globin sequence just 3' of the SP6 promoter, as described by Vu, Cell 64:1057–68 (1991).

After first strand and second strand synthesis from MM6 poly A$^+$ RNA was performed (see subsection 2 above), the cDNA was size selected for 2 kb or greater by agarose gel electrophoresis. BstXI linkers were added for insertion into the pFROG vector. After ligation, pFROG was electroporated into competent MC1061p3 cells. A total of 1,000,000 colonies were screened by hybridization under conditions of high stringency (50% foramide, 6×SSC, 0.1% SDS, 42° C., 16h) as described in Sambrook, *Molecular Cloning: A Laboratory Manual*, Second Edition (1989) using the novel PCR product isolated as described in subsection 2 above. Positives were sequenced using fluorescently labeled dideoxyribonucleotides as described by Sanger, *Proc. Natl. Acad. Sci.* 74:5463 (1977). Two cDNA clones containing the A form of the receptor and two clones containing the B form were isolated.

EXAMPLE 2

Structure of MCP-1R Deduced from the cDNA Sequence

The full sequence of MCP-1RA cDNA (SEQ ID NO:1) and the encoded amino acid sequence (SEQ ID NO:2) are shown in FIGS. 1A–1D. The encoded protein sequence is shown below that of the cDNA sequence. The cDNA sequence (SEQ ID NO:3) and encoded amino acid sequence (SEQ ID NO:4) of MCP-1RB are shown in FIGS. 2A–2C. Conventional numbering is used.

The translation of both MCP-1R DNAs is most likely initiated at the ATG start codon. This is the only in-frame MET codon in the 5' region of the cDNA. Following the initiating methionine (MET) is an open reading frame encoding a protein of 374 amino acids with a predicted molecular weight of about 42,000 Daltons. By direct comparison with the known transmembrane domains for the MIP-1α/RANTES receptor, the orphan receptor HUMSTSR and the IL-8 receptors 8RA and 8RB, an extra cellular amino terminus of 48 residues is revealed. The transmembrane domains are most likely located at amino acids 49 through 70, 80 through 700, 115 through 136, 154 through 178, 204 through 231, 244 through 268 and 295 through 313. They are indicated in FIG. 4 by the horizonal lines above the sequence groupings (SEQ ID NOS: 2, 5, 6, 7 and 8). The carboxyl tail of 61 amino acids begins with serine at position 314 (see FIGS. 4A–4B).

The MCP-1RB cDNA encodes an amino acid sequence identical to that of MCP-1RA from the MET at position 1 through the arginine at position 313 and including 30 untranslated nucleotides immediately 5' of the initiating MET (see FIGS. 2A–2C). The putative amino acid sequence of MCP-1RB (SEQ ID NO:4) however reveals a completely different cytoplasmic tail than the 61 amino acid cytoplasmic tail of MCP-1RA (SEQ ID NO:2). MCP-1RB has a cytoplasmic tail of 47 amino acids beginning with arginine at amino acid position 314 and ending with leucine at position 360. That alternative splicing occurred at position 313 can be inferred from the sequence identity, including the 5' untranslated sequence, of the two clones and from the characteristic AG sequence located at the putative donor junction between amino acid positions 313–314. In addition, a cDNA common to both A and B forms of MCP-1R hybridized to a single band on Southern blots of human genomic DNA under high stringency conditions, and one cDNA clone from the MM6 library was obtained that contained in tandem both carboxyl-terminal cytoplasmic tails found in MCP-1RA and 1RB, suggesting derivation from incompletely processed RNA. The MCP-1 receptor, MCP-1R, is only the second known example of alternative splicing of the carboxyl tails of receptors in the seven-transmembrane receptor family. Namba, *Nature* 365:166–70 (1993) has reported that the prostaglandin (PG) E2 receptor has four alternatively spliced carboxyl-terminal tails with little sequence homology among the four. The related MIP-1α/RANTES and IL-8 receptors are believed to be intronless. See Holmes, *Science* 253:1278–80(1991); Murphy, *Science* 253:1280–83(1991) and Neote, *Cell* 72:415–25 (1993). Alignment of the cytoplasmic tails of MCP-1RA and 1RB with other chemokine receptors revealed that one of the receptors, MCP-1RB, was homologous to the corresponding region in the MIP-1α/RANTES receptor. The carboxyl tail of MCP-1RA bore no significant identity with other known proteins.

Figure 3B:
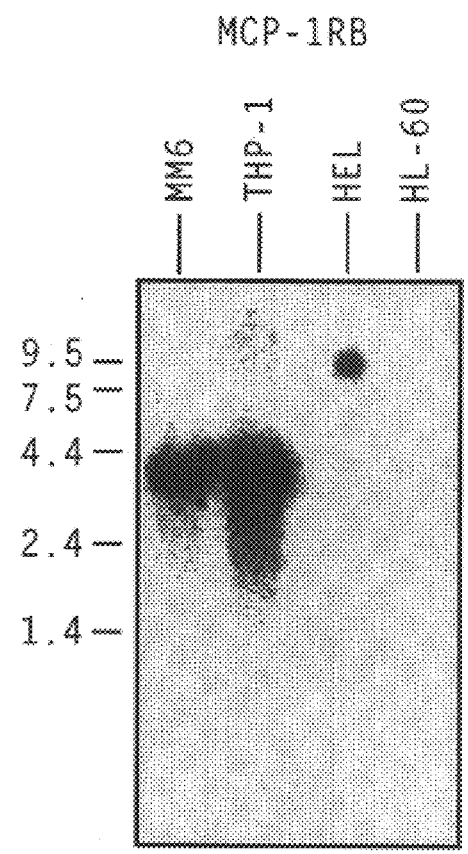
Figure 5:
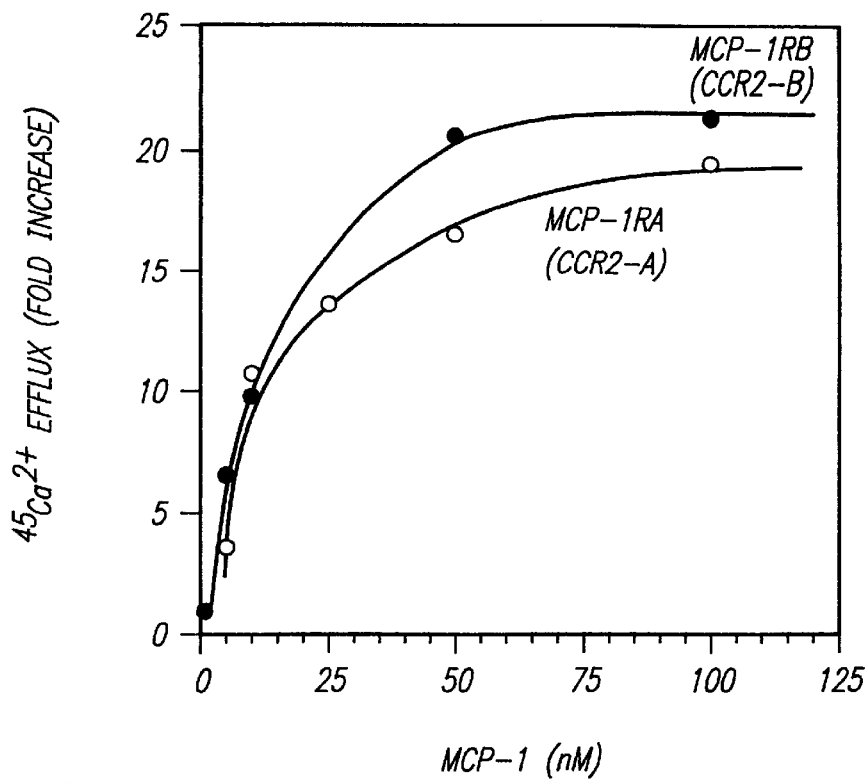

Northern blots of hematopoietic cell lines were performed as described in Sambrook, *Molecular Cloning: A Laboratory Manual*, Second Edition (1989), and probed for each of the MCP-1R clones revealed that both mRNA species migrated as a single 3.5 kb band. See FIGS. 3A–3B. Both mRNAs were expressed at approximately equal levels in the MCP-1 responsive cell lines MM6 and in THP-1 cells. Neither were expressed in the unresponsive cell lines HEL and HL-60. Expression of each of the mRNA was also detected in freshly isolated human monocytes by reverse transcription PCR.

EXAMPLE 3

Similarity of MCP-1RA and 1RB to Other Seven Member Transmembrane Receptors

Comparison of the sequences of MCP-1RA (SEQ ID NO:2) with the IL-8 receptors RA and RB, the MIP-1α/RANTES receptor and the orphan receptor HUMSTSR (SEQ ID NOS:7, 8, 5 and 6, respectively) is illustrated in FIGS. 4A–4B. Comparison of the deduced amino acid sequence of the novel MCP-1A receptor with other seven transmembrane proteins revealed that it most closely relates to the MIP-1α/RANTES receptor, with 51% identity at the amino acid level. The IL-8 receptors RA and RB exhibited 30% identity at the amino acid level to and the HUMSTSR orphan receptor exhibited 31% identity at the amino acid level. Analysis reveals that the MCP-1 receptor has diverged from the related MIP-1α/RANTES receptor and the IL-8 receptors in its amino-terminal and carboxyl-terminal domains. A striking identity between the MCP-1A receptor and the MIP-1α/RANTES receptor is found in the sequence IFFHLLTI DRYLAIV HAVFAL(K/R) ARTVTFGV (SEQ ID NOS: 13 and 14), which occurs at the end of the third transmembrane domain (see FIGS. 4A–4B). The corresponding region of rhodopsin is known to participate in G-protein binding (Franke et al., *Science* 250:123 (1990)), suggesting that this domain may mediate aspects of G-protein activation common to receptors for C-C chemokines.

EXAMPLE 4

Confirmation of Receptor Activity

The calcium efflux assay was performed to confirm expression of functional MCP-1R protein and to determine whether the MCP-1 receptors A and B conferred responsiveness to MCP-1 or other chemokines. In this assay, MCP-1RA and 1RB cRNA was microinjected into Xenopus oocytes and receptor signaling activities measured by detection of agonist-induced calcium mobilization. Signaling activity by the MIP-1α/RANTES receptor and the IL-8 receptor RA was examined in parallel.

Figure 6:
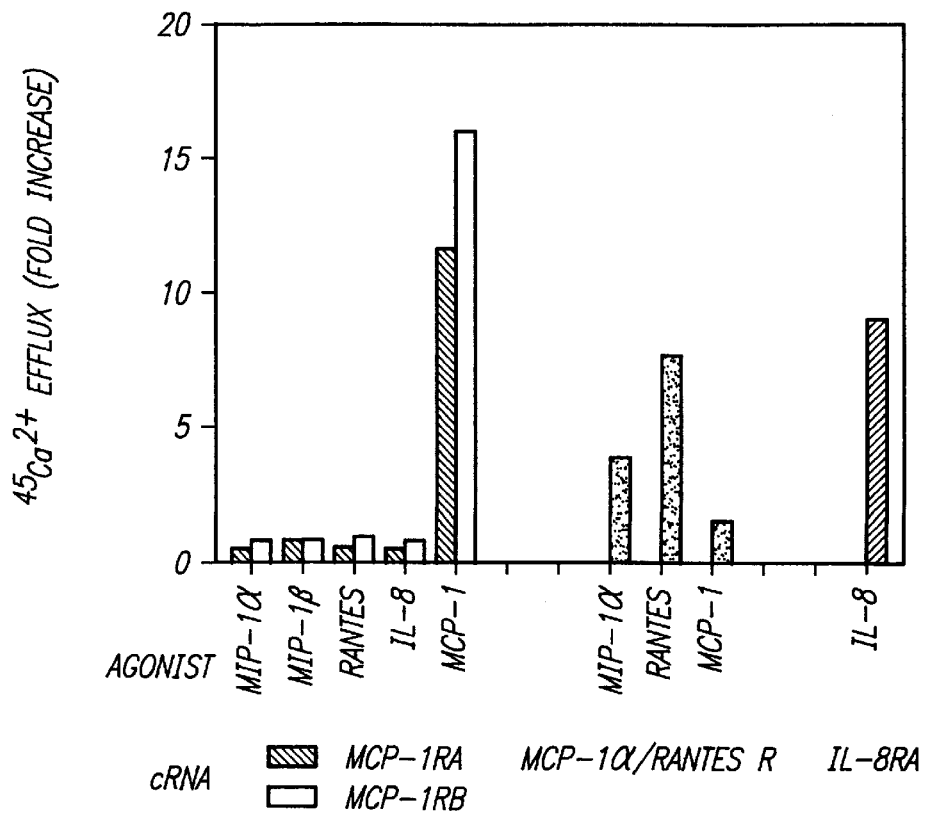

As described in Vu, *Cell* 64:1057–68(1991), cRNA was prepared by SP6 RNA polymerase transcription from a NotI linearized vector and run on an agarose gel to confirm a single band of the expected size. One day after harvesting, oocytes were injected with 20 ng of cRNA in a total volume of 50 nl per oocyte. After incubation in modified Barth's buffer for 2 days at 16° C., the oocytes were loaded with $Ca^{45}$ (50 uCi/ml, Amersham, Arlington Heights, Virginia) for 3 hours, washed for one hour, and placed into wells of a 24-well dish in groups of seven, in a volume of 0.5 ml $Ca^{45}$ efflux was determined by collecting the media at 10 minute intervals and counting beta emissions in a liquid scintillation counter. After a stable baseline had been achieved, cytokine agonists MIP-1α, MIP-1β, RANTES, IL-8 and MCP-1 were added in the Barth's media to the oocytes for 10 minutes. Uninjected oocytes were used as controls. The cytokines, MIP-1α, MIP-1β, RANTES, IL-8 and MCP-1 were obtained from R&D Inc., Minneapolis, Minn. The results are shown in FIG. 6.

Both MCP-1RA and 1RB conferred robust and remarkably specific responses to nanomolar concentrations of MCP-1. No response was elicited by the chemokines MIP-1α, MIP-1β, RANTES, or IL-8, even when these ligands were present at 500 nM. In contrast, the MIP-1α/RANTES receptor signaled in response to MIP-1α and RANTES, but not to MCP-1, consistent with published results. The $EC_{50}$ for MCP-1 was 15 nM.

EXAMPLE 5

MCP-1R Ligand Specificity and Signal Transduction

A. Ligand Specificity

A cell line stably expressing an MCP-1R receptor was produced by transfection of MCP-1RB cDNA into HEK-293 cells.

Human embryo kidney (HEK)-293 (CRL 1573) cells were obtained from the American Type Culture Collection (Bethesda, Md.) and were grown in Minimal Essential Media with Earle's Balanced Salt Solution (MEM-EBSS;GIBCO/BRL, Grand Island, N.Y.) supplemented with 10% fetal calf serum ("FCS") (Hyclone Laboratories Inc., Logan, Utah) and 1% penicillin/streptomycin, at 37° C. in a humidified 5% $CO_2$ atmosphere. cDNAs for the MCP-1 receptor, MCP-1RB, and the MIP-1α/RANTES receptor were cloned into the polylinker of the mammalian cell expression vector pcDNA3 (Invitrogen Inc., San Diego, Calif.) and transfected into 293 cells (50–80% confluent) with a DNA/Lipofectamine (GIBCO/BRL) mixture according to the manufacturer's instructions. After selection for 2–3 weeks in the presence of G418 (0.8 mg/ml) (GIBCO/BRL), colonies were picked and stable cell lines were screened by northern blot analysis for receptor expression. In general, there was a strong correlation between the level of receptor expression as judged by northern blot analysis and the strength of the receptor signals obtained in the below described functional assays. Transfected cells that failed to express the receptor on northern blots were used as negative controls in the binding and signaling experiments.

Figure 7A:
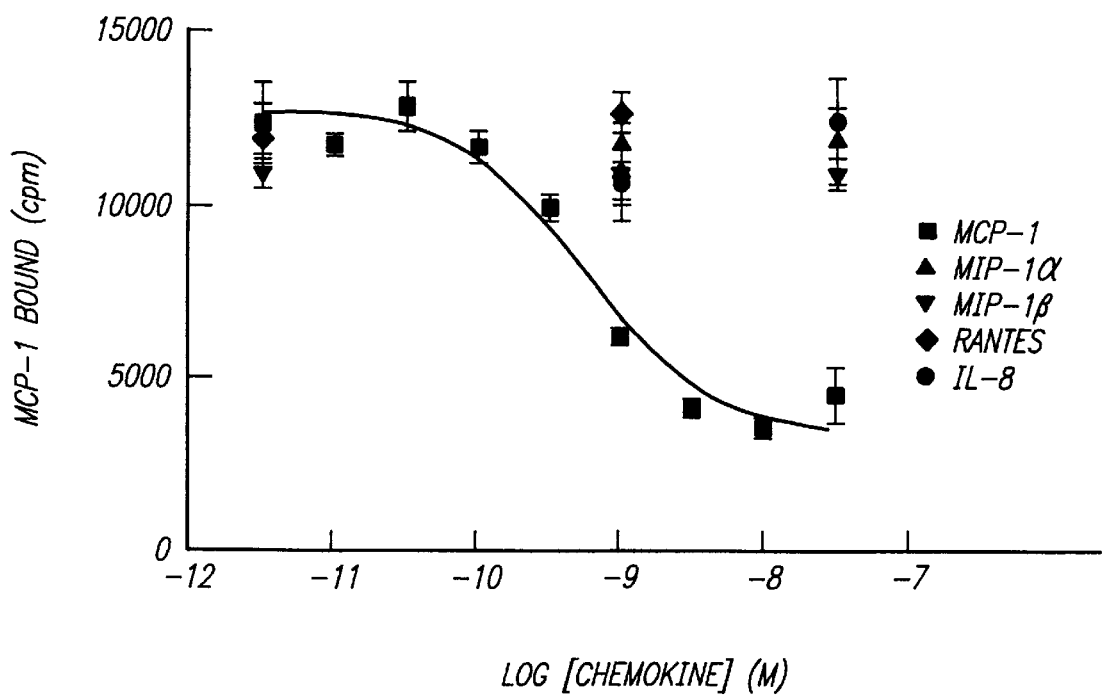
Figure 7B:
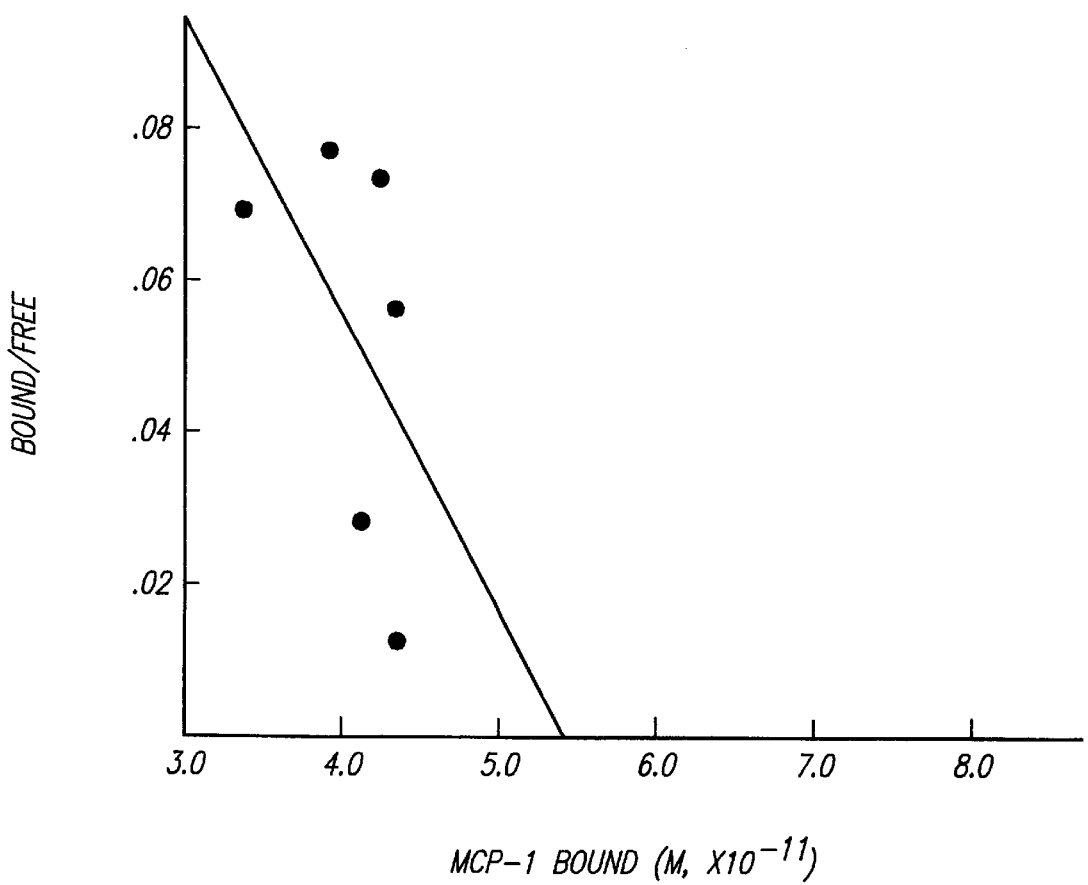

Equilibrium binding assays were then performed using the method of Ernst, *J. Immunol.* 152: 3541–49 (1994). Varying amounts of $^{125}$I-labeled MCP-1 (Dupont-NEN, Boston, Mass.) were incubated with $6 \times 10^6$ MCP-1RB expressing HEK-293 cells resuspended in binding buffer (50 mM Hepes, pH 7.2, 1 mM $CaCl_2$, 5 mM $MgCl_2$, 0.5% BSA (bovine serum albumin, fraction V, Sigma)) in the presence or absence of 100-fold excess of the unlabeled C-C chemokines MIP-1α, MIP-1β and RANTES, and the C-X-C chemokine IL-8 (chemokines obtained from R&D Systems, Inc., Minneapolis, Minn). Competition experiments were performed using 500 pM $^{125}$I-labeled MCP-1 and the concentrations of unlabeled chemokines as indicated in FIGS. 7A–7B.

Equilibrium binding data were analyzed according to the method of Scatchard using the program "LIGAND" (Biosoft, Ferguson, Mo.) on a Macintosh computer. See Munson, *Anal. Biochem.* 107: 220–39 (1980). The closely related C-C chemokines MIP-1α, MIP-1β, and RANTES, as well as the C-X-C chemokine IL-8 did not compete for binding. Nor was specific binding detected in transfectants that expressed little or no MCP-1RB on Northern blots. Analysis of equilibrium binding data shown in FIG. 7 indicates a dissociation constant ($K_d$) of 260 pM (FIG. 7B). This $K_d$ is in good agreement with that reported for the binding of MCP-1 to monocytes (Yoshimura, *J. Immunol.* 145:292–97 (1990); Zhang, *J. Biol. Chem.* 269:15918–24 (1994)) and THP-1 cells (Van Riper, *J. Exp. Med.* 177:851–56 (1933)). These data indicate that $^{125}$I-MCP-1 bound specifically and with high affinity to the MCP-1RB receptor expressed in 293 cells.

B. Sienal Transduction

Calcium mobilization in 293 cells was then investigated. Transfected HEK-293 cells were grown until confluent, trypsinized briefly, washed with phosphate buffered saline containing 1 mg/ml BSA (PBS-BSA), and resuspended in serum-free MEM-EBSS supplemented with 1 mg/ml BSA and 10 mM HEPES (pH 7.0) at a density of $2 \times 10^7$ cells/ml. The cells were incubated in the dark at 37° C. for 20 min in the presence of 5–10 μg/ml indo-1 AM (Molecular Probes, Inc., Eugene, Oreg.). Nine volumes of PGS-BSA were added, and the cells were incubated for an additional 10 min at 37° C., pelleted by centrifugation, and washed twice with 50 ml of the PBS-BSA solution. Washed, indo-1-loaded cells were then resuspended in Hank's Balanced Salt Solution (1.3 mM $Ca^{2+}$) supplemented with 1 mg/ml BSA (HBS-BSA) at a density of approximately $0.5 \times 10^6$ cells/ml at room temperature. To measure intracellular calcium ($[Ca^{2+}]_i$), 0.5 ml of the cell suspension was placed in a quartz cuvette in a Hitachi F-2000 fluorescence spectrophotometer. Chemokines (MCP-1, RANTES, MIP-1α, MIP-1β, Gro-α and IL-8) dissolved in HBS-BSA were injected directly into the cuvette in 5 μl volumes. Intracellular calcium was measured by excitation at 350 nm and fluorescence emission detection at 490 nm (F1) and 410 nm (F2) wavelengths. The $[Ca^{2+}]_i$ was estimated by comparing the 490/410 fluorescence ratio after agonist application (R) to that of calibration ratios measured at the end of each run, according to the equation:

$$[Ca^{2+}]_i = K_d \times [(R-R_{min})/(R_{max}-R)] \times (Sf2/Sb2)$$

where $R_{max}$ and $R_{min}$ represent the fluorescence ratio under saturating (1.3 mM $Ca^{2+}$) and nominally free (10 mM EGTA, Sigma Chemical Co.) calcium conditions, $K_d$ is the dissociation constant of calcium for indo-1, R is the fluorescence ratio, and Sf2/Sb2 is the fluorescence ratio of free and bound indo-1 dye at 410 nm. See Thomas, A P and Delaville, F (1991) in *Cellular Calcium, a Practical Approach*, Oxford Univ. Press, pp. 1–54.

To quantitate calcium responses, MCP-1 dose response curves were generated in each experiment and the results were expressed as a percent of the maximum calcium signal (at 300 nM MCP-1) measured in that experiment. The changes in $[Ca^{2+}]_i$ levels in response to each concentration of agonist were determined by subtracting the baseline from peak $[Ca^{2+}]_i$ levels, which were determined by averaging 5 seconds of data prior to agonist addition and surrounding the peak response, respectively. In experiments done to determine the role of extracellular calcium, 3 mM EGTA was added 60–90 seconds prior to MCP-1. Subsequent lysis of the cells with Triton X-100 (Sigma) caused no change in indo-1 fluorescence, indicating that EGTA had reduced the extracellular calcium concentration below that of intracellular basal levels (approximately 70–100 nM). All experiments were performed at room temperature.

Figure 8A:
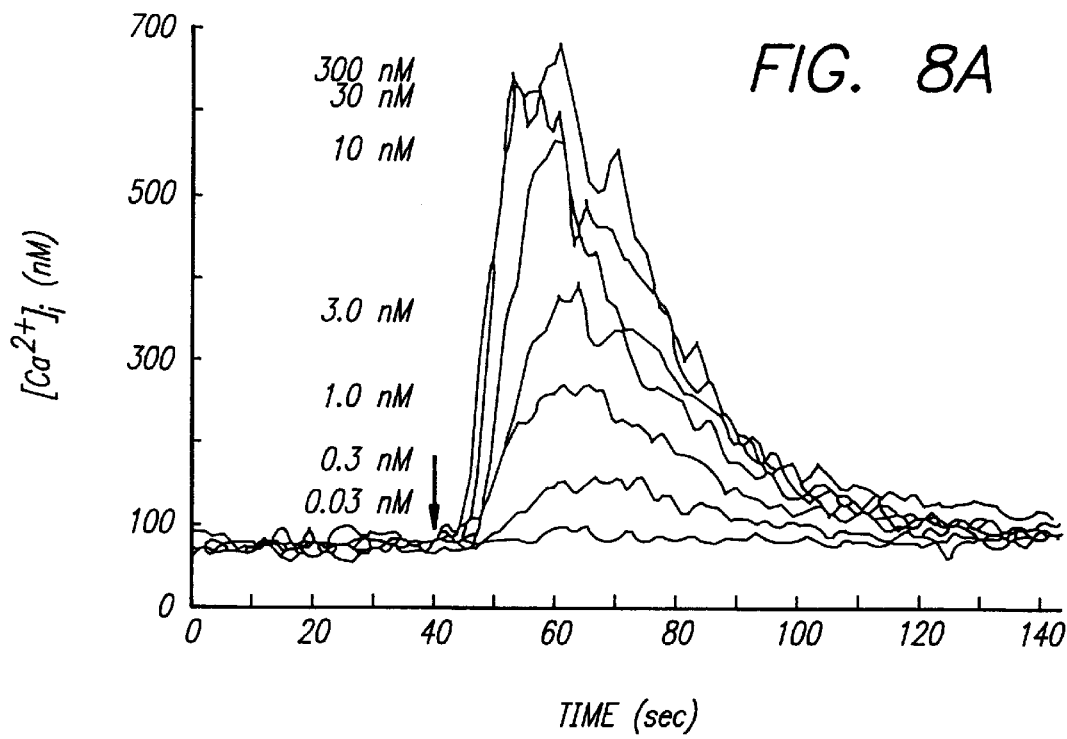
Figure 8B:
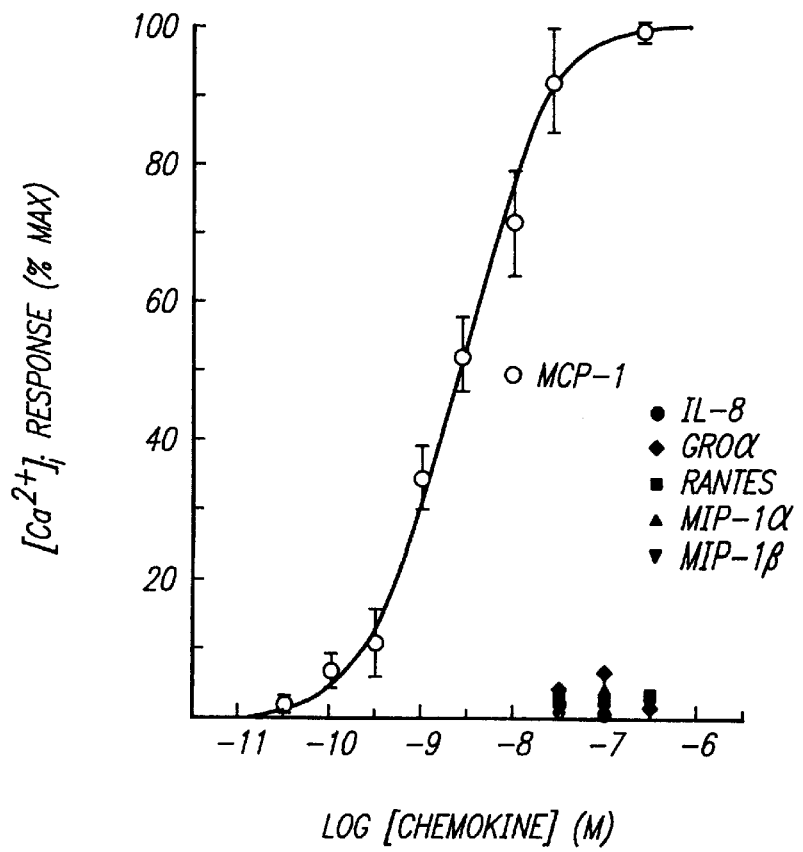
Figure 8C:
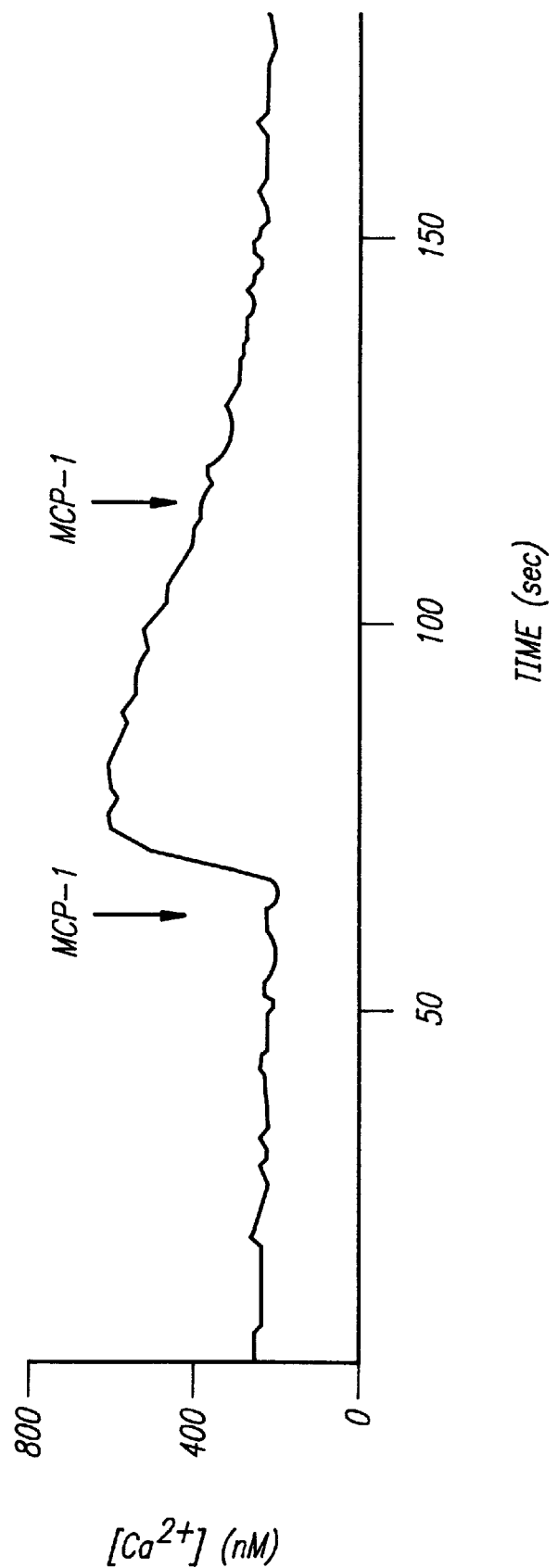

MCP-1 stimulated robust calcium mobilization in the stably transfected MCP-1RB/293 cells in a specific and dose-dependent manner. Small but reproducible signals were seen with as little as 100 pM MCP-1, and the average $EC_{50}$ from four full dose-response curves to MCP-1 was 3.4 nM (2.7–4.4 nM; FIGS. 8A and 8B). The MCP-1RB receptor was selectively activated by MCP-1. RANTES, MIP-1α, MIP-1β, Gro-α, and IL-8 failed to stimulate significant calcium signals in these same cells, even when present at high concentrations (FIG. 8B). Furthermore, these chemokines also failed to block stimulation of the cells by MCP-1, indicating that they are unlikely to act as endogenous antagonists of the MCP-1RB receptor. The MCP-1-dependent intracellular calcium fluxes were characterized by short lag times, followed by a rapid rise in $[Ca^{2+}]_i$ that returned to near basal levels within 80–90 sec of the addition of MCP-1 (FIG. 8A). The cells demonstrated homologous desensitization in that they were refractory to activation by a second challenge with MCP-1 (FIG. 8C).

To determine the source of the intracellular calcium flux, the MCP-1RB/293 cells were challenged with MCP-1 in the presence or absence of extracellular calcium. The rise in cytoplasmic calcium was largely unchanged by the chelation of extracellular calcium with 3 mM EGTA. Similar results were seen when the cells were washed and resuspended in calcium-free PBS supplemented with 1 mM EGTA, or when 5 mM $Ni^{2+}$ was added to the cuvette to block the influx of extracellular calcium. Sozani, *J. Immunol.* 147:2215–21 (1991); Saga, *J. Biol. Chem.* 262:16364–69 (1987). The fall in cytoplasmic calcium to baseline was slightly prolonged in the presence of extracellular calcium, suggesting that calcium influx may contribute to maintaining the response to MCP-1 after intracellular stores are depleted. These data suggest that the primary means of calcium mobilization in these transfected 293 cells is through release of intracellular calcium.

Inositol (1,4,5)-triphosphate ($IP_3$) mobilizes intracellular calcium in response to activation of a wide spectrum of receptors, including many seven-transmembrane-domain receptors. Hung, *J. Cell. Biol.* 116:827–32 (1992); Putney, *Trends Endocrinol. Metab.* 5:256–60 (1994). To investigate this mobilization, total inositol phosphate accumulation was determined as described in Hung, *J. Cell Biol.* 116: 827–32 (1992). HEK-293 cells were grown until confluent in 24-well tissue culture dishes and labeled overnight with 2 uCi/ml [$^3$H]myo-inositol (23 Ci/mmol) (New England Nuclear, Boston, Mass.) in inositol-free MEM-EBSS supplemented with 10% dialyzed FCS. Following labeling, the media were removed and the cells were incubated at room temperature for 5–10 min in 0.5 ml of serum-free MEM-EBSS media supplemented with 10 mM HEPES, 1 mg/ml BSA, and 10 mM LiCl. The washed cells were then incubated with the chemokines MCP-1, MIP-1α, MIP-1β, RANTES, IL-8 and Gro-α for 1–30 min at room temperature in the presence of 10 mM LiCl. The incubation was terminated by removal of the incubation media and addition of 1 ml of ice-cold 20 mM formic acid. Plates were incubated at 4° C. for 30 min before the supernatants were applied to 1-ml Dowex AG1-X8 (100–200 mesh, formate form, from Sigma) chromatography columns. Columns were washed with 8 ml of water followed by 5 ml of 40 mM sodium formate. Total [$^3$H]inositol phosphates were eluted with 5 ml of 2 M ammonium formate/0.1 M formic acid and quantitated by liquid scintillation spectroscopy. Activation of the MCP-1 receptor in transfected 293 cells induced little or no hydrolysis of phosphatidyl inositol. In control experiments activation of the muscarinic (Lameh, *J. Biol. Chem.* 267:13406–412 (1992)) or oxytocin receptor, Kimura, *Nature* 356:526–29 (1992), co-transfected into these same 293 cells, led to a 5- to 9-fold increase in PI turnover.

To investigate inhibition of adenylyl cyclase activity, HEK-293 cells stably-transfected with the MCP-1RB receptor and the MIP-1α/RANTES receptor were grown until confluent in 24-well tissue culture dishes and labeled overnight with 2 μCi/ml of [$^3$H]adenine (25–30 Ci/mmol) (New England Nuclear, Boston, Mass.) in MEM-EBSS supplemented with 10% FCS. The next day, the cells were washed by incubation at room temperature with 0.5 ml of serum-free MEM-EBSS media supplemented with 10 mM HEPES, 1 mg/ml BSA, and 1 mM IBMX (3-isobutyl-1-methylxanthine) for 5 min. After removal of the wash media the cells were stimulated by addition of fresh media containing either chemokine (MCP-1, MIP-1α, MIP-1β, RANTES, IL-8 and Gro-α) alone, forskolin alone (10 μM, Sigma Chemical Co., St. Louis, Mo.), or chemokine plus forskolin, all in the presence of 1 mM IBMX, for 20 min at room temperature. The incubation was terminated by replacement of the media with 1 ml of ice-cold 5% TCA (trichloroacetic acid), 1 mM cAMP, and 1 mM ATP (Sigma). Following incubation at 4° C. for 30 min, the labeled [$^3$H]ATP and [3H]cAMP pools were separated and quantitated by chromatography on Dowex 50W (200–400 mesh, hydrogen form, from Sigma) and neutral alumina columns (also from Sigma), as described in Hung, *J. Biol. Chem.* 267: 20831–34 (1992) and Wong, *Nature* 351: 63–65 (1991). The 1 ml acid supernatant was loaded onto a 1-ml Dowex 50W column and the ATP pool eluted with 3 ml of H$_2$O. The Dowex 50W columns were then placed over 1-ml alumina columns, and 10 ml of H$_2$O was added to the Dowex resin and the eluant allowed to drop directly onto the neutral alumina. The cAMP pool was then eluted directly from the alumina with 5 ml of 0.1 M imidazole/0.01 mM sodium azide. The [$^3$]ATP and [$^3$H]cAMP fractions were counted by liquid scintillation spectroscopy. The cAMP pool for each sample was normalized to its own ATP pool and expressed as a ratio by the equation (cAMP cpms/ATP cpms)×100. In each experiment full dose-response curves were generated and expressed as a percent of the forskolin control.

Activation of the MCP-1 receptor resulted in a potent and dose-dependent inhibition of adenylyl cyclase activity. MCP-1 significantly reduced basal cAMP accumulation in these cells by 55% (p<0.01, Student's t test). Forskolin activation of adenylyl cyclase increased cAMP levels 16-fold, and co-addition of MCP-1 blocked this increase by 78%, with an IC$_{50}$ of 90 mM (70–140 pM). The magnitude and potency of MCP-1 inhibition of adenylyl cyclase activity was independent of the forskolin concentration (3–30 μM). MCP-1 neither stimulated nor inhibited cAMP formation in untransfected or pcDNA3 transfected 293 cell controls.

Together these results demonstrate that inhibition of adenylyl cyclase activity provides a sensitive and quantitative assay for MCP-1RB receptor activation in 293 cells. Virtually no activation of the MCP-1 receptor could be detected in this assay in response to high concentrations of RANTES, MIP-1α, MIP-1β, IL-8, or Gro-α which is consistent with our observations in the calcium fluorimetric assay and in Xenopus oocytes (Example 5).

In similar experiments the MIP-1α/RANTES receptor was stably transfected into 293 cells and also found to mediate potent and dose-dependent inhibition of adenylyl cyclase activity. Unlike the MCP-1RB receptor, however, the MIP-1α/RANTES receptor was activated by multiple chemokines with varying degrees of potency. MIP-1α and RANTES were virtually equipotent in inhibiting adenylyl cyclase activity with IC$_{50}$s of 110 pM and 140 pM, respectively. MIP-1β (IC$_{50}$=820 nM) also inhibited adenylyl cyclase activity, though only at much higher concentrations, and neither blocked cAMP accumulation to the same extent as MIP-1α and RANTES. The C-X-C chemokines IL-8 and Gro-α did not activate the MIP-1α/RANTES receptor at up to 1 μM.

Table I below compares the activation of the MCP-1 receptor and the MIP-1α/RANTES receptor by a variety of chemokines and demonstrates the specificity of the MCP-1RB receptor for MCP-1, and the MIP-1α/RANTES receptor for MIP-1α and RANTES. Neither of the C-X-C chemokines was active on either of the two cloned C—C chemokine receptors.

TABLE I

Specificity of the MCP-1 and MIP-1α/RANTES Receptors Inhibition of Adenylyl Cyclase

| | MCP-1RB IC$_{50}$ (nM) | MIP-1α/ RANTES R | Selectivity |
|---|---|---|---|
| MCP-1 | .090 | 820 | >9000 for MCP-1R |
| MIP-1α | >10$^3$ | .110 | >9000 for MIP-1α/RANTES R |
| RANTES | >10$^3$ | .140 | >7000 for MIP-1α/RANTES R |
| MIP-1β | >10$^3$ | 10 | >100 for MIP-1α/RANTES R |
| Gro-α | >10$^3$ | >10$^3$ | |
| IL-8 | >10$^3$ | >10$^3$ | |

In all experiments, the maximum inhibition of adenylyl cylase activity mediated by the MCP-1RB or MIP-1α/RANTES receptor was ~80% and ~55%, respectively. Qualitatively similar signaling, manifested by the rapid rise in cytoplasmic calcium and potent inhibition of adenylyl cyclase, was observed in 293 cells expressing the MCP-1RA receptor.

C. Inhibition of MCP-1R Activation

Inhibition of MCP-1RB receptor activation by bordetella pertussis toxin was investigated. Pertussis toxin (List Biological Labs, Inc., Campbell, Calif.) was dissolved in 0.01 M sodium phosphate, pH 7.0, 0.05 M sodium chloride and diluted into normal serum containing media at final concentrations of 0.1 ng/ml to 100 ng/ml, and incubated with cells overnight (14–16 h) at 37° C. The conditions of the Pertussis toxin treatment of the 293 cells were identical for calcium fluorimetric and adenylyl cyclase experiments. In the adenylyl cyclase experiments, the Pertussis toxin was added at the same time as [$^3$H]adenine.

The MCP-1-induced mobilization of intracellular calcium, as well as the inhibition of adenylyl cyclase, was substantially blocked by pretreatment of cells with bordetella pertussis toxin. Dose-response studies indicated a similar degree of inhibition of these two pathways by pertussis toxin, as well as a component (≈20%) that was resistant to inhibition by up to 100 ng/ml of PT. The effect of pertussis toxin treatment was to reduce the magnitude of the MCP-1 inhibition of cAMP accumulation without significantly shifting the MCP-1 IC$_{50}$, a result consistent with the hypothesis that pertussis toxin treatment functionally uncouples the MCP-1RB receptor from Gαi. These results also suggest that both the inhibition of adenylyl cyclase activity and the mobilization of intracellular calcium may be mediated through activation of the same G-protein in the 293 cells.

D. Discussion of Results

MCP-1 induced a rapid rise in intracellular calcium in indo-1-loaded 293 cells that were stably transfected with MCP-1RB. The stable cell line also demonstrated dose-dependent homologous desensitization of calcium mobilization in response to MCP-1. The relative contributions of extracellular and intracellular calcium stores to this calcium flux has been controversial. The results above support the conclusion that the initial rise in cytoplasmic calcium after activation of the MCP-1 receptor in 293 cells is almost exclusively due to the release of intracellular calcium stores. First, chelation of extracellular calcium with EGTA (2 mM to 10 mM) had little effect on the rise and peal levels of the calcium transients, but did hasten the return to baseline calcium levels. Second, the same result was obtained when the transfected cells were incubated in calcium-free media, supplemented with 1 mM EGTA. Finally, virtually identical results were obtained in the presence of 5 mM $Ni^{2+}$, which blocks the influx of extracellular calcium.

Activation of the MCP-1RB receptor led to profound inhibition of adenylyl cyclase, suggesting coupling via one of the isoforms of Gαi. Similar results were obtained using the cloned MIP-1α/RANTES receptor, indicating that at least two of the receptors for C-C chemokines activate Gαi. Moreover, pertussis toxin blocked both the calcium mobilization as well as the inhibition of adenylyl cyclase induced by MCP-1. Similarity in the pertussis toxin dose-response curves for calcium mobilization and inhibition of adenylyl cyclase suggests that both may be downstream consequences of coupling to Gαi. These studies are the first demonstration of adenylyl cyclase inhibition by chemokine receptors, and are consistent with reports that leukocyte chemotaxis to IL-8, fMLP and MCP-1 is sensitive to inhibition by pertussis toxin. Oppenheim, *Ann. Rev. Immunol.* 9: 617–48 (1991); Spangrude, *J.Immunol.* 135: 4135–43 (1985); Sozzini, *J. Immunol.* 147: 2215–21 (1991).

Although inhibition of adenylyl cyclase is the most thoroughly characterized downstream effect of the activation of Gαi in leukocytes, Gαi has also been implicated in the activation of potassium channels, in the induction of mitosis and in the activation of Ras and microtubule associated protein (MAP) kinase in fMLP stimulated neutrophils. Yatani, *Nature* 336:680–82 (1988); Seuwan, *J. Biol. Chem.* 265: 22292–99 (1990); Worthen, *J. Clin. Invest.* 94:815–23 (1994). Thus, activation of Gαi may activate a complex array of intracellular signals that ultimately lead to leukocyte activation and chemotaxis.

A pertussis toxin-sensitive signal transduction pathway in which βγ dimers, released in conjunction with Gαi, activate the $β_2$ isoform of the phospholipase C (PLC$β_2$) to generate $IP_3$ has been described. Wu, *Science* 261:101–031. Cellular activation via this pathway would be expected to result in a pertussis toxin-sensitive mobilization of intracellular calcium. However, 293 cells stably expressing the recombinant MCP-1 receptor hydrolyze little, if any PI (phosphatydlinositol) when challenged with MCP-1. In control experiments, Gq-coupled receptors, co-transfected into this cell line, increased total inositol phosphates 5- to 9-fold upon activation. The failure to detect PI turnover in the MCP-1RB transfected cells suggests that the MCP-1 receptor mobilizes intracellular calcium via a novel mechanism independent of $IP_3$.

MCP-1RB was remarkably specific for MCP-1. In the cyclase assay the $IC_{50}$ for inhibition by MCP-1 was 90 pM, whereas related chemokines were ineffective at up to 1 μM. In contrast, the MIP-1-α/RANTES receptor has an IC50 of approximately 100 pM for MIP-1α and RANTES, and 10 nM and 820 nM for MIP-1β and MCP-1, respectively. Thus, MCP-1 had a selectivity of at least 9000-fold for the MCP-1 receptor, whereas MIP-1α and RANTES had a similar preference for the MIP-1-α/RANTES receptor, as compared to MCP-1RB. It is likely, therefore, that under physiological conditions, MCP-1, MIP-1α, and RANTES act as specific agonists of MCP-1RB and the MIP-1-α/RANTES receptor, respectively.

The $IC_{50}$ for MCP-1-medicated inhibition of adenylyl cyclase was approximately 90 pM, well below the dissociation constant for binding ($K_d$=260 pM) which suggests that relatively few receptors must be occupied for efficient coupling to Gαi. In contrast, very high receptor occupancy was required to elicit peak intracellular calcium fluxes ($EC_{50}$= 2–4 nM). It is interesting to note, in this regard, that the $EC_{50}$ for monocyte chemotaxis to MCP-1 is subnanomolar. Yoshimura, *J. Immunol.* 145:292–97 (1990). Thus the induction of chemotaxis, which is the hallmark function of MCP-1 is optimal at MCP-1 concentrations that provide for efficient coupling/signaling through Gαi but are insufficient to elicit maximal intracellular calcium fluxes and subsequent receptor desensitization, suggesting that modest increases in intracellular calcium are sufficient to initiate and support monocyte chemotaxis. The high levels of intracellular calcium detected at nanomolar concentrations of MCP-1 may serve to stop monocyte migration by desensitizing the receptor and unregulating adhesion molecules.

MCP-1 is synthesized and secreted in vitro by a number of different cells in response to a variety of different cytokines or oxidatively modified lipoproteins. The specificity of the cloned receptor for MCP-1, coupled with the fact that only monocytes, basophils, and a subset of T lymphocytes response to MCP-1, provides for an effective means of limiting the spectrum of infiltrating leukocytes in areas where MCP-1 is abundant. Early atherosclerotic lesions have a predominantly monocytic infiltrate and MCP-1 is abundant in these lesions. In contrast, the MIP-1-α/RANTES receptor binds and signals in response to multiple chemokines, and may serve to mediate more complex inflammatory reactions. Once activated, however, the MCP-1 and MIP-1-α/RANTES receptors appear to use similar signal transduction pathways.

Dose response curves generated in the calcium fluorimetric and adenylyl cyclase inhibition assays were fit by a nonlinear least squares program to the logistic equation:

$$\text{Effect=max effect}/[1+(EC_{50}/(\text{agonist})^n)]$$

where n and $EC_{50}$ represent the Hill coefficient and the agonist concentration that elicited a half-maximal response, respectively, and were derived from the fitted curve. Curve fitting was done with the computer program "Prism" (by Graph Pad, San Diego, Calif.). Results represent the mean ±SE. The 95% confidence intervals (CI) of the $EC_{50}$ and $IC_{50}$ values, when given, were calculated from the log $EC_{50}$ and $IC_{50}$ values, respectively.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:

1. An isolated polypeptide comprising the amino acid sequence of an MCP-1R polypeptide which is
   (a) a polypeptide having a sequence at least 90% identical to the sequence of MCP-1RA as shown in SEQ ID NO: 2,
   (b) a polypeptide having a sequence at least 90% identical to the sequence of MCP-1RB as shown in SEQ ID NO: 4, or
   (c) a fragment of a polypeptide according to (a) or (b) which binds specifically to MCP-1, wherein the sequence of the fragment is at least 90% identical to the corresponding portion of SEQ ID NO: 2 or SEQ ID NO: 4;

wherein the MCP-1R polypeptide binds specifically to MCP-1 but not to MIP-1α, MIP-1β, RANTES, or IL-8 under physiological conditions.

2. An isolated polypeptide according to claim 1, wherein the polypeptides (a) and (b) and the fragment (c) are at least 95% identical to SEQ ID NO: 2, SEQ ID NO: 4, and the corresponding portion of SEQ ID NO: 2 or SEQ ID NO: 4, respectively.

3. An isolated polypeptide according to claim 1, comprising the amino acid sequence of an MCP-1R polypeptide having a sequence at least 90% identical to the sequence shown in SEQ ID NO: 2 or SEQ ID NO: 4.

4. An isolated polypeptide according to claim 3, comprising the amino acid sequence of an MCP-1R polypeptide having a sequence at least 95% identical to the sequence shown in SEQ ID NO: 2 or SEQ ID NO: 4.

5. An isolated polypeptide according to any one of claims 1 to 4, free of association with other polypeptides.

6. A polypeptide free of association with other polypeptides, wherein the polypeptide comprises the amino acid sequence shown in SEQ ID NO: 2 or SEQ ID NO: 4.

7. An isolated nucleic acid molecule comprising a nucleotide sequence encoding the amino acid sequence of an MCP-1R polypeptide according to claim 1.

8. An isolated nucleic acid molecule comprising a nucleotide sequence encoding the amino acid sequence of an MCP-1R polypeptide according to claim 2.

9. A nucleic acid molecule according to claim 8, wherein the polypeptides (a) and (b) have the amino acid sequences shown in SEQ ID NOs: 2 and 4, respectively.

10. An isolated nucleic acid molecule comprising a nucleotide sequence encoding the amino acid sequence of an MCP-1R polypeptide according to claim 3.

11. An isolated nucleic acid molecule comprising a nucleotide sequence encoding the amino acid sequence of an MCP-1R polypeptide according to claim 4.

12. An isolated nucleic acid molecule comprising a nucleotide sequence encoding the amino acid sequence shown in SEQ ID NO: 2.

13. A nucleic acid molecule according to claim 12, comprising the nucleotide sequence shown as residues 50 to 1161 of SEQ ID NO: 1.

14. A nucleic acid molecule according to claim 13, comprising the entire nucleotide sequence shown in SEQ ID NO: 1.

15. An isolated nucleic acid molecule comprising a nucleotide sequence encoding the amino acid sequence shown in SEQ ID NO: 4.

16. A nucleic acid molecule according to claim 15, comprising the nucleotide sequence shown as residues 81 to 1160 of SEQ ID NO: 3.

17. A nucleic acid molecule according to claim 16, comprising the entire nucleotide sequence shown in SEQ ID NO: 3.

18. An isolated nucleic acid molecule encoding an MCP-1R polypeptide, wherein the nucleic acid molecule comprises (a) the nucleotide sequence of an MCP-1R cDNA that is present in a mammalian library and that hybridizes under stringent conditions with a probe having the sequence of the complement of the coding sequence shown in SEQ ID NO: 1 or SEQ ID NO: 3, wherein the cDNA encodes an MCP-1R polypeptide that binds specifically to MCP-1 but not to MIP-1α, MIP-1β, RANTES, or IL-8 under physiological conditions;

(b) the nucleotide sequence of a fragment of an MCP-1R cDNA according to (a), wherein a polypeptide having the MCP-1R amino acid sequence encoded by the fragment binds specifically to MCP-1; or (c) a nucleotide sequence degenerate with (a) or (b).

19. A nucleic acid molecule according to claim 18, comprising the nucleotide sequence of said MCP-1R cDNA.

20. An expression vector comprising the nucleotide sequence of a nucleic acid molecule according to any one of claims 7 to 19.

21. A mammalian, insect, or yeast cell comprising heterologous nucleic acid having the sequence of a molecule according to any one of claims 7 to 19, wherein the cell is capable of effecting replication and expression of the heterologous nucleic acid.

22. A cell according to claim 21, wherein the MCP-1R polypeptide encoded by the heterologous nucleic acid is stably expressed on the surface of the cell.

23. A process for producing an MCP-1R polypeptide, comprising culturing a cell according to claim 21 under conditions suitable to effect expression of the heterologous nucleic acid.

24. A process according to claim 23, further comprising the step of isolating the expressed MCP-1R polypeptide from the cell.

25. A method to identify an agonist or antagonist of MCP-1R, comprising:

(a) contacting a cell according to claim 22 with MCP-1 in the presence and absence of a candidate organic compound, and (b) comparing the binding of the MCP-1 to the MCP-1R polypeptide in the presence of the compound to the binding of the MCP-1 to the MCP-1R polypeptide in its absence;

wherein a compound which causes an increase in the binding of MCP-1 to the MCP-1R polypeptide is identified as an agonist of MCP-1R, and a compound which causes a decrease in the binding of MCP-1 to the MCP-1R polypeptide is identified as an antagonist of MCP-1R.

26. A method according to claim 25, wherein the compound causes a decrease in the binding of MCP-1 to the MCP-1R polypeptide.

27. A method according to claim 25, wherein the MCP-1 is detectably labeled.

28. A method according to claim 25, wherein the binding of MCP-1 to the MCP-1R polypeptide is determined in an immunoassay.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 2232 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 40..1161

(xi) SEQUENCE DESCRIPTION: SEQ ID NO:1:

```
GGATTGAACA AGGACGCATT TCCCCAGTAC ATCCACAAC ATG CTG TCC ACA TCT       54
                                            Met Leu Ser Thr Ser
                                             1               5

CGT TCT CGG TTT ATC AGA AAT ACC AAC GAG AGC GGT GAA GAA GTC ACC     102
Arg Ser Arg Phe Ile Arg Asn Thr Asn Glu Ser Gly Glu Glu Val Thr
             10                  15                  20

ACC TTT TTT GAT TAT GAT TAC GGT GCT CCC TGT CAT AAA TTT GAC GTG     150
Thr Phe Phe Asp Tyr Asp Tyr Gly Ala Pro Cys His Lys Phe Asp Val
             25                  30                  35

AAG CAA ATT GGG GCC CAA CTC CTG CCT CCG CTC TAC TCG CTG GTG TTC     198
Lys Gln Ile Gly Ala Gln Leu Leu Pro Pro Leu Tyr Ser Leu Val Phe
         40                  45                  50

ATC TTT GGT TTT GTG GGC AAC ATG CTG GTC GTC CTC ATC TTA ATA AAC     246
Ile Phe Gly Phe Val Gly Asn Met Leu Val Val Leu Ile Leu Ile Asn
     55                  60                  65

TGC AAA AAG CTG AAG TGC TTG ACT GAC ATT TAC CTG CTC AAC CTG GCC     294
Cys Lys Lys Leu Lys Cys Leu Thr Asp Ile Tyr Leu Leu Asn Leu Ala
 70                  75                  80                  85

ATC TCT GAT CTG CTT TTT CTT ATT ACT CTC CCA TTG TGG GCT CAC TCT     342
Ile Ser Asp Leu Leu Phe Leu Ile Thr Leu Pro Leu Trp Ala His Ser
             90                  95                 100

GCT GCA AAT GAG TGG GTC TTT GGG AAT GCA ATG TGC AAA TTA TTC ACA     390
Ala Ala Asn Glu Trp Val Phe Gly Asn Ala Met Cys Lys Leu Phe Thr
            105                 110                 115

GGG CTG TAT CAC ATC GGT TAT TTT GGC GGA ATC TTC TTC ATC ATC CTC     438
Gly Leu Tyr His Ile Gly Tyr Phe Gly Gly Ile Phe Phe Ile Ile Leu
        120                 125                 130

CTG ACA ATC GAT AGA TAC CTG GCT ATT GTC CAT GCT GTG TTT GCT TTA     486
Leu Thr Ile Asp Arg Tyr Leu Ala Ile Val His Ala Val Phe Ala Leu
    135                 140                 145

AAA GCC AGG ACG GTC ACC TTT GGG GTG GTG ACA AGT GTG ATC ACC TGG     534
Lys Ala Arg Thr Val Thr Phe Gly Val Val Thr Ser Val Ile Thr Trp
150                 155                 160                 165

TTG GTG GCT GTG TTT GCT TCT GTC CCA GGA ATC ATC TTT ACT AAA TGC     582
Leu Val Ala Val Phe Ala Ser Val Pro Gly Ile Ile Phe Thr Lys Cys
                170                 175                 180

CAG AAA GAA GAT TCT GTT TAT GTC TGT GGC CCT TAT TTT CCA CGA GGA     630
Gln Lys Glu Asp Ser Val Tyr Val Cys Gly Pro Tyr Phe Pro Arg Gly
            185                 190                 195
```

```
TGG AAT AAT TTC CAC ACA ATA ATG AGG AAC ATT TTG GGG CTG GTC CTG        678
Trp Asn Asn Phe His Thr Ile Met Arg Asn Ile Leu Gly Leu Val Leu
        200                 205                 210

CCG CTG CTC ATC ATG GTC ATC TGC TAC TCG GGA ATC CTG AAA ACC CTG        726
Pro Leu Leu Ile Met Val Ile Cys Tyr Ser Gly Ile Leu Lys Thr Leu
        215                 220                 225

CTT CGG TGT CGA AAC GAG AAG AAG AGG CAT AGG GCA GTG AGA GTC ATC        774
Leu Arg Cys Arg Asn Glu Lys Lys Arg His Arg Ala Val Arg Val Ile
230                 235                 240                 245

TTC ACC ATC ATG ATT GTT TAC TTT CTC TTC TGG ACT CCC TAT AAC ATT        822
Phe Thr Ile Met Ile Val Tyr Phe Leu Phe Trp Thr Pro Tyr Asn Ile
                250                 255                 260

GTC ATT CTC CTG AAC ACC TTC CAG GAA TTC TTC GGC CTG AGT AAC TGT        870
Val Ile Leu Leu Asn Thr Phe Gln Glu Phe Phe Gly Leu Ser Asn Cys
            265                 270                 275

GAA AGC ACC AGT CAA CTG GAC CAA GCC ACG CAG GTG ACA GAG ACT CTT        918
Glu Ser Thr Ser Gln Leu Asp Gln Ala Thr Gln Val Thr Glu Thr Leu
            280                 285                 290

GGG ATG ACT CAC TGC TGC ATC AAT CCC ATC ATC TAT GCC TTC GTT GGG        966
Gly Met Thr His Cys Cys Ile Asn Pro Ile Ile Tyr Ala Phe Val Gly
295                 300                 305

GAG AAG TTC AGA AGC CTT TTT CAC ATA GCT CTT GGC TGT AGG ATT GCC       1014
Glu Lys Phe Arg Ser Leu Phe His Ile Ala Leu Gly Cys Arg Ile Ala
310                 315                 320                 325

CCA CTC CAA AAA CCA GTG TGT GGA GGT CCA GGA GTG AGA CCA GGA AAG       1062
Pro Leu Gln Lys Pro Val Cys Gly Gly Pro Gly Val Arg Pro Gly Lys
                330                 335                 340

AAT GTG AAA GTG ACT ACA CAA GGA CTC CTC GAT GGT CGT GGA AAA GGA       1110
Asn Val Lys Val Thr Thr Gln Gly Leu Leu Asp Gly Arg Gly Lys Gly
            345                 350                 355

AAG TCA ATT GGC AGA GCC CCT GAA GCC AGT CTT CAG GAC AAA GAA GGA       1158
Lys Ser Ile Gly Arg Ala Pro Glu Ala Ser Leu Gln Asp Lys Glu Gly
            360                 365                 370

GCC TAGAGACAGA AATGACAGAT CTCTGCTTTG AAATCACAC GTCTGGCTTC              1211
Ala

ACAGATGTGT GATTCACAGT GTGAATCTTG GTGTCTACGT TACCAGGCAG AAGGCTGAG       1271

AGGAGAGAGA CTCCAGCTGG GTTGGAAAAC AGTATTTTCC AAACTACCTT CCAGTTCCTC      1331

ATTTTTGAAT ACAGGCATAG AGTTCAGACT TTTTTTAAAT AGTAAAAATA AAATTAAAGC      1391

TGAAAACTGC AACTTGTAAA TGTGGTAAAG AGTTAGTTTG AGTTGCTATC ATGTCAAACG      1451

TGAAAATGCT GTATTAGTCA CAGAGATAAT TCTAGCTTTG AGCTTAAGAA TTTTGAGCAG      1511

GTGGTATGTT TGGAGACTG CTGAGTCAAC CCAATAGTTG TTGATTGGCA GGAGTTGGAA       1571

GTGTGTGATC TGTGGGCACA TTAGCCTATG TGCATGCAGC ATCAAGTAA TGATGTCGTT       1631

TGAATCACAG TATACGCTCC ATCGCTGTCA TCTCAGCTGG ATCTCCATTC TCTCAGGCTT      1691

GCTGCCAAAA GCCTTTTGTG TTTTGTTTTG TATCATTATG AAGTCATGCG TTTAATCACA      1751

TTCGAGTGTT TCAGTGCTTC GCAGATGTCC TTGATGCTCA TATTGTTCCC TAATTTGCCA      1811

GTGGGAACTC CTAAATCAAA TTGGCTTCTA ATCAAAGCTT TTAAACCCTA TTGGTAAAGA      1871

ATGGAAGGTG GAGAAGCTCC CTGAAGTAAG CAAAGACTTT CCTCTTAGTC GAGCCAAGTT      1931

AAGAATGTTC TTATGTTGCC CAGTGTGTTT CTGATCTGAT GCAAGCAAGA AACACTGGGC      1991

TTCTAGAACC AGGCAACTTG GGAACTAGAC TCCCAAGCTG GACTATGGCT CTACTTTCAG      2051

GCCACATGGC TAAAGAAGGT TTCAGAAAGA AGTGGGGACA GAGCAGAACT TTCACCTTCA      2111

TATATTTGTA TGATCCTAAT GAATGCATAA AATGTTAAGT TGATGGTGAT GAAATGTAAA      2171
```

TACTGTTTTT AACAACTATG ATTTGGAAAA TAAATCAATG CTATAACTAT GTTGATAAAA    2231

G    2232

(2) INFORMATION FOR SEQ ID NO:2:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Ser Thr Ser Arg Ser Arg Phe Ile Arg Asn Thr Asn Glu Ser
 1               5                  10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
 50                  55                  60

Leu Ile Leu Ile Asn Cys Lys Lys Leu Lys Cys Leu Thr Asp Ile Tyr
 65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335
```

```
Val Arg Pro Gly Lys Asn Val Lys Val Thr Thr Gln Gly Leu Leu Asp
        340                 345                 350

Gly Arg Gly Lys Gly Lys Ser Ile Gly Arg Ala Pro Glu Ala Ser Leu
        355                 360                 365

Gln Asp Lys Glu Gly Ala
        370

(2) INFORMATION FOR SEQ ID NO:3:

(i) SEQUENCE CHARACTERISTICS:
        (A) LENGTH: 1979 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 81..1160

(xi) SEQUENCE DESCRIPTION: SEQ ID NO:3:

CAGGACTGCC TGAGACAAGC CACAAGCTGA ACAGAGAAAG TGGATTGAAC AAGGACGCAT        60

TTCCCCAGTA CATCCACAAC ATG CTG TCC ACA TCT CGT TCT CGG TTT ATC          110
                     Met Leu Ser Thr Ser Arg Ser Arg Phe Ile
                       1               5                  10

AGA AAT ACC AAC GAG AGC GGT GAA GAA GTC ACC ACC TTT TTT GAT TAT        158
Arg Asn Thr Asn Glu Ser Gly Glu Glu Val Thr Thr Phe Phe Asp Tyr
                15                  20                  25

GAT TAC GGT GCT CCC TGT CAT AAA TTT GAC GTG AAG CAA ATT GGG GCC        206
Asp Tyr Gly Ala Pro Cys His Lys Phe Asp Val Lys Gln Ile Gly Ala
            30                  35                  40

CAA CTC CTG CCT CCG CTC TAC TCG CTG GTG TTC ATC TTT GGT TTT GTG        254
Gln Leu Leu Pro Pro Leu Tyr Ser Leu Val Phe Ile Phe Gly Phe Val
        45                  50                  55

GGC AAC ATG CTG GTC GTC CTC ATC TTA ATA AAC TGC AAA AAG CTG AAG        302
Gly Asn Met Leu Val Val Leu Ile Leu Ile Asn Cys Lys Lys Leu Lys
    60                  65                  70

TGC TTG ACT GAC ATT TAC CTG CTC AAC CTG GCC ATC TCT GAT CTG CTT        350
Cys Leu Thr Asp Ile Tyr Leu Leu Asn Leu Ala Ile Ser Asp Leu Leu
 75                  80                  85                  90

TTT CTT ATT ACT CTC CCA TTG TGG GCT CAC TCT GCT GCA AAT GAG TGG        398
Phe Leu Ile Thr Leu Pro Leu Trp Ala His Ser Ala Ala Asn Glu Trp
                 95                 100                 105

GTC TTT GGG AAT GCA ATG TGC AAA TTA TTC ACA GGG CTG TAT CAC ATC        446
Val Phe Gly Asn Ala Met Cys Lys Leu Phe Thr Gly Leu Tyr His Ile
            110                 115                 120

GGT TAT TTT GGC GGA ATC TTC TTC ATC ATC CTC CTG ACA ATC GAT AGA        494
Gly Tyr Phe Gly Gly Ile Phe Phe Ile Ile Leu Leu Thr Ile Asp Arg
        125                 130                 135

TAC CTG GCT ATT GTC CAT GCT GTG TTT GCT TTA AAA GCC AGG ACG GTC        542
Tyr Leu Ala Ile Val His Ala Val Phe Ala Leu Lys Ala Arg Thr Val
    140                 145                 150

ACC TTT GGG GTG GTG ACA AGT GTG ATC ACC TGG TTG GTG GCT GTG TTT        590
Thr Phe Gly Val Val Thr Ser Val Ile Thr Trp Leu Val Ala Val Phe
155                 160                 165                 170

GCT TCT GTC CCA GGA ATC ATC TTT ACT AAA TGC CAG AAA GAA GAT TCT        638
Ala Ser Val Pro Gly Ile Ile Phe Thr Lys Cys Gln Lys Glu Asp Ser
```

-continued

```
                     175                 180                 185
GTT TAT GTC TGT GGC CCT TAT TTT CCA CGA GGA TGG AAT AAT TTC CAC    686
Val Tyr Val Cys Gly Pro Tyr Phe Pro Arg Gly Trp Asn Asn Phe His
            190                 195                 200

ACA ATA ATG AGG AAC ATT TTG GGG CTG GTC CTG CCG CTG CTC ATC ATG    734
Thr Ile Met Arg Asn Ile Leu Gly Leu Val Leu Pro Leu Leu Ile Met
            205                 210                 215

GTC ATC TGC TAC TCG GGA ATC CTG AAA ACC CTG CTT CGG TGT CGA AAC    782
Val Ile Cys Tyr Ser Gly Ile Leu Lys Thr Leu Leu Arg Cys Arg Asn
            220                 225                 230

GAG AAG AAG AGG CAT AGG GCA GTG AGA GTC ATC TTC ACC ATC ATG ATT    830
Glu Lys Lys Arg His Arg Ala Val Arg Val Ile Phe Thr Ile Met Ile
235                 240                 245                 250

GTT TAC TTT CTC TTC TGG ACT CCC TAT AAC ATT GTC ATT CTC CTG AAC    878
Val Tyr Phe Leu Phe Trp Thr Pro Tyr Asn Ile Val Ile Leu Leu Asn
            255                 260                 265

ACC TTC CAG GAA TTC TTC GGC CTG AGT AAC TGT GAA AGC ACC AGT CAA    926
Thr Phe Gln Glu Phe Phe Gly Leu Ser Asn Cys Glu Ser Thr Ser Gln
            270                 275                 280

CTG GAC CAA GCC ACG CAG GTG ACA GAG ACT CTT GGG ATG ACT CAC TGC    974
Leu Asp Gln Ala Thr Gln Val Thr Glu Thr Leu Gly Met Thr His Cys
            285                 290                 295

TGC ATC AAT CCC ATC ATC TAT GCC TTC GTT GGG GAG AAG TTC AGA AGG   1022
Cys Ile Asn Pro Ile Ile Tyr Ala Phe Val Gly Glu Lys Phe Arg Arg
            300                 305                 310

TAT CTC TCG GTG TTC TTC CGA AAG CAC ATC ACC AAG CGC TTC TGC AAA   1070
Tyr Leu Ser Val Phe Phe Arg Lys His Ile Thr Lys Arg Phe Cys Lys
315                 320                 325                 330

CAA TGT CCA GTT TTC TAC AGG GAG ACA GTG GAT GGA GTG ACT TCA ACA   1118
Gln Cys Pro Val Phe Tyr Arg Glu Thr Val Asp Gly Val Thr Ser Thr
            335                 340                 345

AAC ACG CCT TCC ACT GGG GAG CAG GAA GTC TCG GCT GGT TTA           1160
Asn Thr Pro Ser Thr Gly Glu Gln Glu Val Ser Ala Gly Leu
            350                 355                 360

TAAAACGAGG AGCAGTTTGA TTGTTGTTTA TAAAGGGAGA TAACAATCTG TATATAACAA  1220

CAAACTTCAA GGGTTTGTTG AACAATAGAA ACCTGTAAAG CAGGTGCCCA GGAACCTCAG  1280

GGCTGTGTGT ACTAATACAG ACTATGTCAC CCAATGCATA TCCAACATGT GCTCAGGGAA  1340

TAATCCAGAA AAACTGTGGG TAGAGACTTT GACTCTCCAG AAAGCTCATC TCAGCTCCTG  1400

AAAAATGCCT CATTACCTTG TGCTAATCCT CTTTTTCTAG TCTTCATAAT TTCTTCACTC  1460

AATCTCTGAT TCTGTCAATG TCTTGAAATC AAGGGCCAGC TGGAGGTGAA AAGAGAATG   1520

TGACAGGCAC AGATGAATGG GAGTGAGGGA TAGTGGGGTC AGGGCTGAGA GGAGAAGGAG  1580

GGAGACATGA GCATGGCTGA GCCTGGACAA AGACAAAGGT GAGCAAAGGG CTCACGCATT  1640

CAGCCAGGAG ATGATACTGG TCCTTAGCCC CATCTGCCAC GTGTATTTAA CCTTGAAGGG  1700

TTCACCAGGT CAGGGAGAGT TTGGGAACTG CAATAACCTG GGAGTTTTGG TGGAGTCCGA  1760

TGATTCTCTT TTGCATAAGT GCATGACATA TTTTTGCTTT ATTACAGTTT ATCTATGGCA  1820

CCCATGCACC TTACATTTGA AATCTATGAA ATATCATGCT CCATTGTTCA GATGCTTCTT  1880

AGGCCACATC CCCCTGTCTA AAAATTCAGA AAATTTTTGT TTATAAAAGA TGCATTATCT  1940

ATGATATGCT AATATATGTA TATGCAATAT AAAATTTAG                        1979
```

(2) INFORMATION FOR SEQ ID NO:4:

(i) SEQUENCE CHARACTERISTICS:
        (A) LENGTH: 360 amino acids (B) TYPE: amino acid
(D) TOPOLOGY: linear (ii) MOLECULE TYPE: protein (xi) SEQUENCE DESCRIPTION: SEQ ID NO:4:

```
Met Leu Ser Thr Ser Arg Ser Arg Phe Ile Arg Asn Thr Asn Glu Ser
  1               5                  10                  15

Gly Glu Glu Val Thr Thr Phe Phe Asp Tyr Asp Tyr Gly Ala Pro Cys
                 20                  25                  30

His Lys Phe Asp Val Lys Gln Ile Gly Ala Gln Leu Leu Pro Pro Leu
             35                  40                  45

Tyr Ser Leu Val Phe Ile Phe Gly Phe Val Gly Asn Met Leu Val Val
         50                  55                  60

Leu Ile Leu Ile Asn Cys Lys Lys Leu Lys Cys Leu Thr Asp Ile Tyr
 65                  70                  75                  80

Leu Leu Asn Leu Ala Ile Ser Asp Leu Leu Phe Leu Ile Thr Leu Pro
                 85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
            340                 345                 350

Glu Gln Glu Val Ser Ala Gly Leu
        355                 360
```

(2) INFORMATION FOR SEQ ID NO:5:

(i) SEQUENCE CHARACTERISTICS:
    (A) LENGTH: 355 amino acids
    (B) TYPE: amino acid
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

```
Met Glu Thr Pro Asn Thr Thr Glu Asp Tyr Asp Thr Thr Thr Glu Phe
 1               5                  10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Leu Val Leu Val Gln Tyr Lys Arg
    50                  55                  60

Leu Lys Asn Met Thr Ser Ile Tyr Leu Leu Asn Leu Ala Ile Ser Asp
 65                  70                  75                  80

Leu Leu Phe Leu Phe Thr Leu Pro Phe Trp Ile Asp Tyr Lys Leu Lys
                85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
130                 135                 140

Arg Thr Val Thr Phe Gly Val Ile Thr Ser Ile Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285

Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
            340                 345                 350
```

Ala Gly Phe
        355

(2) INFORMATION FOR SEQ ID NO:6:

(i) SEQUENCE CHARACTERISTICS:
        (A) LENGTH: 352 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:6:

Met Glu Gly Ile Ser Ile Tyr Thr Ser Asp Asn Tyr Thr Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Tyr Ile Tyr Ser Ile Ile
                35                  40                  45

Phe Leu Tyr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
                115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Val Phe Gln Phe Gln His Ile Met Val Gly Leu
    195                 200                 205

Ile Leu Pro Gly Ile Val Ile Leu Phe Cys Tyr Cys Ile Ile Ile Ser
    210                 215                 220

Lys Leu Ser His Ser Lys Gly His Gln Lys Arg Lys Ala Leu Lys Tyr
225                 230                 235                 240

Tyr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
                260                 265                 270

Gly Cys Glu Phe Glu Asn Thr Val His Lys Trp Ile Ser Ile Thr Glu
                275                 280                 285

Ala Leu Ala Phe Phe His Cys Cys Leu Asn Pro Ile Leu Tyr Ala Phe
    290                 295                 300

Leu Gly Ala Lys Phe Lys Tyr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340             345             350

(2) INFORMATION FOR SEQ ID NO:7:

(i) SEQUENCE CHARACTERISTICS:
        (A) LENGTH: 350 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:7:

Met Ser Asn Ile Thr Asp Pro Gln Met Trp Asp Phe Asp Asp Leu Asn
1               5                  10                  15

Phe Thr Gly Met Pro Pro Ala Asp Glu Asp Tyr Ser Pro Cys Met Leu
                20                  25                  30

Glu Thr Glu Thr Leu Asn Lys Tyr Val Ile Ile Ala Tyr Ala Leu
            35                  40                  45

Val Phe Leu Leu Ser Leu Leu Gly Asn Ser Leu Val Met Leu Val Ile
50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
                100                 105                 110

Val Ser Leu Leu Lys Glu Val Asn Phe Tyr Ser Gly Ile Leu Leu Leu
                115                 120                 125

Ala Cys Ile Ser Val Asp Arg Tyr Leu Ala Ile Val His Ala Thr Arg
130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
                180                 185                 190

Asn Asp Thr Ala Lys Trp Arg Met Val Leu Arg Ile Leu Pro His Thr
                195                 200                 205

Phe Gly Phe Ile Val Pro Leu Phe Val Met Leu Phe Cys Tyr Gly Phe
                210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
                260                 265                 270

Ile Gln Glu Thr Cys Glu Arg Arg Asn Asn Ile Gly Arg Ala Leu Asp
                275                 280                 285

Ala Thr Glu Ile Leu Gly Phe Leu His Ser Cys Leu Asn Pro Ile Ile
                290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
            325                 330                 335

Thr Ser Tyr Thr Ser Ser Ser Val Asn Val Ser Ser Asn Leu
            340                 345                 350

(2) INFORMATION FOR SEQ ID NO:8:

(i) SEQUENCE CHARACTERISTICS:
      (A) LENGTH: 355 amino acids
      (B) TYPE: amino acid
      (D) TOPOLOGY: linear (ii) MOLECULE TYPE: protein (iii) HYPOTHETICAL: NO (xi) SEQUENCE DESCRIPTION: SEQ ID NO:8:

Met Glu Ser Asp Ser Phe Glu Asp Phe Trp Lys Gly Glu Asp Leu Ser
1               5                   10                  15

Asn Tyr Ser Tyr Ser Ser Thr Leu Pro Pro Phe Leu Leu Asp Ala Ala
            20                  25                  30

Pro Cys Glu Pro Glu Ser Leu Glu Ile Asn Lys Tyr Phe Val Val Ile
        35                  40                  45

Ile Tyr Ala Leu Val Phe Leu Leu Ser Leu Leu Gly Asn Ser Leu Val
50                  55                  60

Met Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Ala Leu Pro Val Leu
                165                 170                 175

Leu Phe Arg Arg Thr Val Tyr Ser Ser Asn Val Ser Pro Ala Cys Tyr
            180                 185                 190

Glu Asp Met Gly Asn Asn Thr Ala Asn Trp Arg Met Leu Leu Arg Ile
        195                 200                 205

Leu Pro Gln Ser Phe Gly Phe Ile Val Pro Leu Leu Ile Met Leu Phe
210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Thr Gln Val Ile Gln Glu Thr Cys Glu Arg Arg Asn His Ile Asp
        275                 280                 285

Arg Ala Leu Asp Ala Thr Glu Ile Leu Gly Ile Leu His Ser Cys Leu
290                 295                 300

Asn Pro Leu Ile Tyr Ala Phe Ile Gly Gln Lys Phe Arg His Gly Leu

```
                305                 310                 315                 320
        Leu Lys Ile Leu Ala Ile His Gly Leu Ile Ser Lys Asp Ser Leu Pro
                        325                 330                 335
        Lys Asp Ser Arg Pro Ser Phe Val Gly Ser Ser Gly His Thr Ser
                        340                 345                 350
        Thr Thr Leu
                355

(2) INFORMATION FOR SEQ ID NO:9:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:9:

CGCTCGAGAC CTRKCMDTKK CYGACCT                                              27

(2) INFORMATION FOR SEQ ID NO:10:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:10:

GCGAATTCTG GACRATGGCC AGGTAVCKGT C                                         31

(2) INFORMATION FOR SEQ ID NO:11:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:11:

Asn Leu Ala Ile Ser Asp Leu
1               5

(2) INFORMATION FOR SEQ ID NO:12:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:12:

Asp Arg Tyr Leu Ala Ile Val
1               5
```

(2) INFORMATION FOR SEQ ID NO:13:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:13:

```
Ile Phe Phe Ile Ile Leu Leu Thr Ile Asp Arg Tyr Leu Ala Ile Val
1               5                   10                  15

His Ala Val Phe Ala Leu Lys Ala Arg Thr Val Thr Phe Gly Val
            20                  25                  30
```

(2) INFORMATION FOR SEQ ID NO:14:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:14:

```
Ile Phe Phe Ile Ile Leu Leu Thr Ile Asp Arg Tyr Leu Ala Ile Val
1               5                   10                  15

His Ala Val Phe Ala Leu Arg Ala Arg Thr Val Thr Phe Gly Val
            20                  25                  30
```